(12) United States Patent
Hanigan

(10) Patent No.: US 8,741,937 B2
(45) Date of Patent: Jun. 3, 2014

(54) GAMMA GLUTAMYL TRANSPEPTIDASE INHIBITORS AND METHODS OF USE

(75) Inventor: Marie H. Hanigan, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 13/428,224

(22) Filed: Mar. 23, 2012

(65) Prior Publication Data

US 2013/0085168 A1    Apr. 4, 2013

Related U.S. Application Data

(63) Continuation-in-part of application No. 12/365,517, filed on Feb. 4, 2009, now abandoned.

(60) Provisional application No. 61/063,525, filed on Feb. 4, 2008.

(51) Int. Cl.
*A01N 43/82*    (2006.01)
*A61K 31/41*    (2006.01)

(52) U.S. Cl.
USPC ............................. 514/363; 514/359; 514/361

(58) Field of Classification Search
USPC .......................................... 514/359, 361, 363
See application file for complete search history.

(56) References Cited

U.S. PATENT DOCUMENTS

| | | | |
|---|---|---|---|
| 5,854,006 A | 12/1998 | Hanigan | |
| 6,617,355 B1 | 9/2003 | Gaston et al. | |
| 7,432,301 B2 | 10/2008 | Gaston et al. | |
| 2005/0009821 A1 | 1/2005 | Pyring et al. | |
| 2007/0066614 A1 | 3/2007 | Pyring et al. | |
| 2010/0197745 A1 * | 8/2010 | Hanigan | 514/363 |

FOREIGN PATENT DOCUMENTS

| | | | | |
|---|---|---|---|---|
| WO | WO 98/49190 | | 11/1998 | |
| WO | WO2004/103980 A1 * | 12/2004 | | C07D 285/08 |
| WO | WO2009/100121 A1 * | 8/2009 | | A61K 31/555 |

OTHER PUBLICATIONS

Townsend et al., "Inhibition of Gamma-Glutamyl Transpeptidase or Cysteine S-Conjugate Beta-Lyase Activity Blocks the Nephrotoxicity of Cisplatin in Mice", *J. Pharm.Exp. Ther.*, (2002) vol. 300, No. 1, pp. 142-148.

Okada et al., "Crystal structures of Gamma-glutamyltranspeptidase from *Escherichia coli*, a key enzyme in glutathione metabolism, and its reaction intermediate", *Proc. Natl. Acad. Sci. USA*, (Apr. 25, 2006), vol. 103, No. 17, pp. 6471-6476.

King et al., "A novel, Species-specific Class of Uncompetitive Inhibitors of (gamma)-Glutamyl Transpeptidase", *J. Bil. Chem. Epub*, (Feb. 2009) vol. 284, No. 14, pp. 9059-9065.

Avetisyan et al., "Synthesis and hypoglycemic activity of sulfonamide-1, 3, 4-thiadiazoles", Khimiko-Farmatsevticheskii Zhurnal, (1981), vol. 15(6):69-72 (Abstract).

Wickham et al., "Divergent effects of compounds on the hydrolysis and transpeptidation reactions of y-glutamyl transpeptidase", (Jun. 2011), Journal of Enzyme Inhibition and Medicinal Chem., 1-14.

PCT/US2009/033063, Hanigan, International Search Report and Written Opinion, May 12, 2009.

Wickham et al., "Inhibition of human y-glutamyl transpeptidase: development of more potent, physiologically relevant, uncompetitive inhibitors," (2013) *Biochem. J.*, vol. 450, pp. 547-557.

U.S. Appl. No. 12/365,517, Hanigan, Preliminary Amendment filed Sep. 1, 2010.

U.S. Appl. No. 12/365,517, Hanigan, Office Action Restriction, dated May 3, 2011.

U.S. Appl. No. 12/365,517, Hanigan, Response to Office Action Restriction, filed Aug. 22, 2011.

U.S. Appl. No. 12/365,517, Hanigan, Office Action, dated Sep. 23, 2011.

U.S. Appl. No. 12/365,517, Hanigan, Express Abandonment, filed Mar. 23, 2012.

* cited by examiner

*Primary Examiner* — My-Chau T Tran
(74) *Attorney, Agent, or Firm* — Dunlap Codding, PC

(57) ABSTRACT

Compositions and methods for inhibiting human gamma-glutamyl transpeptidase (GGT) in vivo or in vitro and for inhibiting and killing neoplastic cancer cells, for example for the treatment, inhibition or prevention of tumors or malignant growths or other neoplasias in mammals, or sensitizing tumor to other therapies including radiation therapy. The GGT inhibitor compounds comprise a class of benzylthiadiazol benzenesulfoniamides. The compounds may also be used to treat a reversible airways obstruction in a mammal or a disease associated with reverse airways obstruction such as asthma, chronic obstructive pulmonary disease (COPD), allergic reaction, respiratory tract infection or upper respiratory tract disease. Other diseases or conditions which may be treated include, for example, degenerative diseases, renal diseases, liver diseases, cardiovascular disease and inner ear conditions or diseases.

22 Claims, 9 Drawing Sheets

Formula I

Formula IIA

Formula IIB

GAMMA GLUTAMYL TRANSPEPTIDASE INHIBITORS AND METHODS OF USE

CROSS-REFERENCE TO RELATED APPLICATIONS

The present application is a continuation-in-part of U.S. Ser. No. 12/365,517 filed Feb. 4, 2009, now abandoned, which claims the benefit under 35 U.S.C. 119(e) of U.S. Provisional Application Ser. No. 61/063,525, filed Feb. 4, 2008, the entirety of which is hereby expressly incorporated herein by reference.

STATEMENT REGARDING FEDERALLY SPONSORED RESEARCH OR DEVELOPMENT

This invention was made with government support under Contract Number CA057530 awarded by the National Institutes of Health. The government has certain rights in the invention.

BACKGROUND OF THE INVENTION

It is widely known that many chemotherapeutic regimens fail because the side-effects of the drugs used limit the dose that can be administered. This is particularly true of solid tumors. The clinically tolerated doses are often insufficient to kill all of the cells, thereby enriching the tumor population for drug resistant mutants. Among the surviving tumor cells in below-effective treatment regimens are mutant cells that arise spontaneously within the tumor cell population, and are resistant to the treatment drug. Each subsequent round of chemotherapy enriches the population for the resistant cells, which grow and continue to mutate, some to even higher levels of resistance. There is an established linear-log relationship between dose and tumor kill. The higher the dose of the drug, the greater the chance of eradicating the tumor. While methods have been developed to selectively target and kill tumor cells, many of the targeting methods either reduce the effectiveness of the drug, or call for a complex series of reactions to prepare a drug.

In the consideration of solid tumors, it should be recognized that local effective dosage, and systemic dosage, need not be the same. Thus, the only effective portion of the chemotherapeutic agent administered is that which reaches the tumor cell. Many chemotherapeutic agents are administered systemically, however, and only a limited portion (the local dosage) of the dosage administered actually reaches the cell. Thus, dose limitations frequently result in only a fraction of the permitted dosage actually reaching the cell.

The mechanism of inherent and acquired resistance of tumors to many forms of treatment involves glutathione. Elevated glutathione levels in tumors have been shown to contribute to resistance to chemotherapy and radiotherapy and prevent the initiation of the apoptotic cascade in tumor cells (1-5). The enzyme γ-glutamyl transpeptidase (GGT, EC 2.3.2.2), which is localized to the cell surface, cleaves the γ-glutamyl bond of extracellular glutathione, releasing glutamic acid and cysteinyl-glycine, thus enabling the cell to use extracellular glutathione as a source of cysteine for increased synthesis of intracellular glutathione (6). GGT is induced in many human tumors, enhancing their resistance to chemotherapy (7; 8) Inhibiting GGT prior to chemotherapy or radiation would sensitize GGT-positive tumors to treatment Inhibiting GGT for as little as 2 hours lowers the intracellular cysteine concentration in GGT-positive tumors (3). However, all known GGT inhibitors, prior to the present invention, are too toxic for use in humans at concentrations needed to inhibit GGT activity (9; 10).

GGT plays an essential role in releasing cysteine from extracellular glutathione. Most cells are unable to take up intact glutathione (6). In GGT knockout mice, the absence of GGT in the renal proximal tubules results in the excretion of glutathione in the urine (11). In these mice, the glutathione in the glomerular filtrate cannot be cleaved into its constituent amino acids for reabsorption. GGT knockout mice have a 4500-fold elevation of glutathione in their urine relative to their GGT-wild-type littermates. GGT knockout mice grow slowly and die by ten weeks of age due to a cysteine deficiency. GGT also metabolizes S-nitroso-glutathione, initiating the release of nitric oxide from S-nitroso-glutathione. Nitric oxide is known to play a role in asthma, vascular diseases and other pathologies. GGT contributes to inflammatory disease by converting leukotriene LTC4 to LTD4. In arthritis GGT stimulates osteoclast formation thereby increasing bone destruction in the joint. Further, GGT is involved in the degradation of glutathione during storage of blood and platelets.

GGT catalyzes the cleavage of γ-glutamyl compounds and the transfer of the gamma-glutamyl group to an acceptor substrate by a ping-pong kinetic mechanism (12). Glutathione and glutathione-S-conjugates are the most common physiologic substrates of GGT. They serve as the gamma-glutamyl donor in the initial reaction. In the first reaction the γ-glutamyl bond of the initial substrate is cleaved, the γ-glutamyl group becomes covalently bound to the enzyme and the remainder of the substrate is released as the first product. With glutathione as the substrate, cysteinyl-glycine is released and is subsequently cleaved into cysteine and glycine by cell surface dipeptidases. In the second reaction of GGT transpeptidation, the γ-glutamyl-group is transferred from the γ-glutamyl-GGT complex to the second substrate (the acceptor). Dipeptides and amino acids have the highest Km as acceptors. The second substrate with the covalently bound gamma-glutamyl group is released as the second product from the enzyme.

Compounds which are known to inhibit GGT include the glutamine analogues acivicin, 6-diazo-5-oxo-L-norleucine, and azaserine (13). Rational design of GGT inhibitors based on studies of the active site has led to the identification of additional γ-glutamyl analogues. Lherbet and Keillor have designed sulfur derivatives of L-glutamic acid which inhibit GGT (14; 15). Han and coworkers have synthesized and tested a series of γ-(monophenyl)phosphono glutamate analogues which also functioned as inhibitors of GGT (16; 17).

Evaluation of several of the glutamine analogues that inhibit GGT has shown them to be toxic (9; 10). Acivicin, the most potent inhibitor of GGT that has been tested clinically, is a neurotoxin (18). The neurotoxicity of the glutamine analogues may be due to interference with glutamine in recycling the neurotransmitter glutamate via the glutamate-glutamine cycle. Glutamine is also involved in the synthesis of several nucleotides and complex polysaccharides. Inhibition of these essential synthetic pathways can be toxic to dividing cells. Acivicin, 6-diazo-5-oxo-L-norleucine, and azaserine all cause bone marrow suppression (9). There is no previously known GGT inhibitor that can be used clinically. Identification of GGT inhibitors which could be used clinically has been a highly desired, yet unmet, need, until the present invention.

Physicians generally prescribe three main treatments for cancer: surgery, radiation therapy, chemotherapy or a combination of these.

Surgery is generally advisable when physicians can safely remove the cancer from the body. In situations where the cancerous cells have spread, surgeons sometimes must remove large areas of healthy tissue along with the tumor to insure that no malignancy remains. In these cases, physicians may remove lymph nodes from the tumor area because cancer can spread through nodes. However, unfortunately many cancers are discovered too late for surgical cure. In many cases, the patient does not experience symptoms until the cancer has progressed to a malignant stage.

Radiation therapy is used to destroy cancer cells. However, radiation can both cause and destroy cancer and can cause damage to surrounding tissues. Side effects of radiation therapy include radiation sickness, which are nausea and skin redness in the tumor area. Reducing the negative side effects of radiation treatment is therefore highly desirable.

Chemotherapy uses drugs that take advantage of cancer cells' rapid growth and consumption of large amounts of nutrients. Chemotherapy side effects include nausea and temporary full or partial hair loss. Antimetabolites, one group of these drugs, work by mimicking the nutrients the body's cells consume. Physicians inject these drugs into the bloodstream, where they travel throughout the body, consumed by every cell. Rapidly growing cancerous cells consume much more of the poisonous drugs than do normal cells. As a result, the drugs destroy cancerous cells faster than normal cells. Another group of chemotherapy drugs interferes with the duplication of DNA (cells reproduce by duplicating their genetic code, or DNA), so cells cannot reproduce. Chemotherapy can also be directed against mutated proteins in the tumor cells, overexpressed proteins or other properties of the tumor cell. Chemotherapy drugs act on all the patients cells, the cancerous cells and the healthy cells. A physician's challenge is to administer the drugs to kill only the cancer cells, not the healthy cells. Side effects such as those described above prevent the long term or recurrent use of these drugs. Furthermore, there are an increasing number of effective drugs that can no longer be used due to resistance by the causative agent. It is thus highly desirable to reduce the side effects of therapeutics while maintaining the cancer-reducing qualities thereof, enabling the longer term use, or use of higher dosages of the drugs.

SUMMARY OF THE INVENTION

In one embodiment, the present invention provides an antitumor agent effect enhancer that assists and enhances the effects of antitumor agents and increases the sensitivity of therapy-resistant tumor cells to antitumor agents. More specifically, the antitumor agent effect enhancer comprises a GGT inhibitor, which enhances the effects of chemotherapeutic agents and/or radiation therapy. The present invention is thus directed to compositions and methods for enhancing the inhibition or killing of neoplastic (cancer) cells, for example for the treatment, inhibition or prevention of tumors or malignant growths or other neoplasias in mammals, including humans The GGT inhibitor compounds used in the methods of the present invention, in one embodiment, comprise a class of benzylthiadiazol benzenesulfoniamides represented by the general structure Formula I (FIG. 1), wherein any one or more of $R_1$-$R_{10}$ may be H, Cl, F, Br, I, OH, an alkoxy, or $NO_2$, or, any two or more of $R_1$-$R_{10}$ may be any combination of H, Cl, F, Br, I, OH, an alkoxy, or $NO_2$. Other R groups include carrier groups linked by C, N, or O. The GGT inhibitor compounds used in the methods of the present invention, in other embodiments, comprise a class of benzylthiadiazol naphthylsulfoniamides represented by the general structures Formula IIA (FIG. 7) and Formula IIB (FIG. 8) wherein any one or more of $R_{11}$-$R_{17}$ may be H, Cl, F, Br, I, OH, an alkoxy, or $NO_2$, or, any two or more of $R_{11}$-$R_{17}$ may be any combination of H, Cl, F, Br, I, OH, an alkoxy, or $NO_2$. Other R groups include carrier groups linked by C, N, or O. Further, in the compounds of either of Formula IIA and Formula IIB one or more of adjacent pairs $R_{11}$ and $R_{12}$, $R_{12}$ and $R_{13}$, $R_{13}$ and $R_{14}$, $R_{15}$ and $R_{16}$, and $R_{16}$ and $R_{17}$, may comprise a benzene ring. For example, a benzene ring between the pair $R_{12}$ and $R_{13}$ of Formula IIA would form the naphthylsulfoniamide group into an anthracylsulfoniamide and a benzene ring between the pair $R_{13}$ and $R_{14}$ of Formula IIB would form the naphthylsulfoniamide group into an anthracylsulfoniamide.

In one embodiment, the present invention is directed to a method of enhancing the efficacy of an anticancer therapy in a subject having a cancer, comprising administering to the subject a GGT inhibitor of the classes represented by Formula I, IIA, or IIB, or a pharmaceutically acceptable salt thereof, and administering an anticancer therapy (chemotherapy and/or radiation therapy) to the subject, wherein the efficacy of the anticancer therapy is enhanced, for example by reducing resistance to the drug and sensitizing the tumor cells to apoptosis thereby enabling use of a higher dosage of the anticancer therapy, and/or by reducing the toxicity of the anticancer therapy.

The present invention also provides a method for the prophylaxis or treatment of a reversible airways obstruction in a mammal, such as a human, comprising administration of a therapeutically effective amount of a compound of Formula I, IIA, or IIB, or a pharmaceutically acceptable salt, thereof, for the prophylaxis or treatment of a disease associated with reverse airways obstruction such as asthma, chronic obstructive pulmonary disease (COPD), allergic reaction, respiratory tract infection or upper respiratory tract disease.

Other embodiments of the invention will become apparent upon review of the present description.

DETAILED DESCRIPTION OF THE INVENTION

The present invention is directed to compositions and methods for enhancing the inhibition of neoplastic (cancer) cells, for example for the treatment, inhibition or prevention of tumors or malignant growths or other neoplasias in mammals. The present invention also provides a method for the prophylaxis or treatment of a reversible airways obstruction in a mammal, such as a human, comprising administration of a therapeutically effective amount of a compound of Formula I, IIA, or IIB, or a pharmaceutically acceptable salt, thereof, for the prophylaxis or treatment of a disease associated with reverse airways obstruction such as asthma, chronic obstructive pulmonary disease (COPD), allergic reaction, respiratory tract infection or upper respiratory tract disease. Other conditions or diseases which may be treated include renal and liver diseases, cardiovascular disease, inner ear diseases and conditions, and degenerative diseases.

Expression of gamma-glutamyl transpeptidase (GGT) in neoplastic tumors contributes to resistance of tumors to radiation and chemotherapy. GGT has numerous roles in the body including enabling cells to use extracellular glutathione as a source of additional cysteine. Inhibitors of GGT activity could be used prior to (or with) the administration of chemotherapy to limit the supply of cysteine to the tumor, thereby blocking the tumor's ability to maintain high levels of intracellular glutathione.

However, as noted above, GGT inhibitors that have been evaluated previously in clinical trials have been found to be too toxic for use in humans. For example, acivicin, a well-characterized GGT inhibitor, causes bone marrow suppression, neurological and gastrointestinal toxicity. The present invention is thus directed to clinical use of a new class of GGT inhibitors which can be used to sensitize tumors to radiation and chemotherapy. These compounds are uncompetitive inhibitors, binding only after formation of the enzyme-substrate complex. Unlike acivicin and most other known inhibitors of GGT, these compounds are not glutamine analogs.

The compounds used in the present invention comprise a novel class of uncompetitive inhibitors of GGT that are structurally distinct from and less toxic than the glutamine analogues. This new class of compounds occupies the acceptor site, not the γ-glutamyl site.

Figure 7:
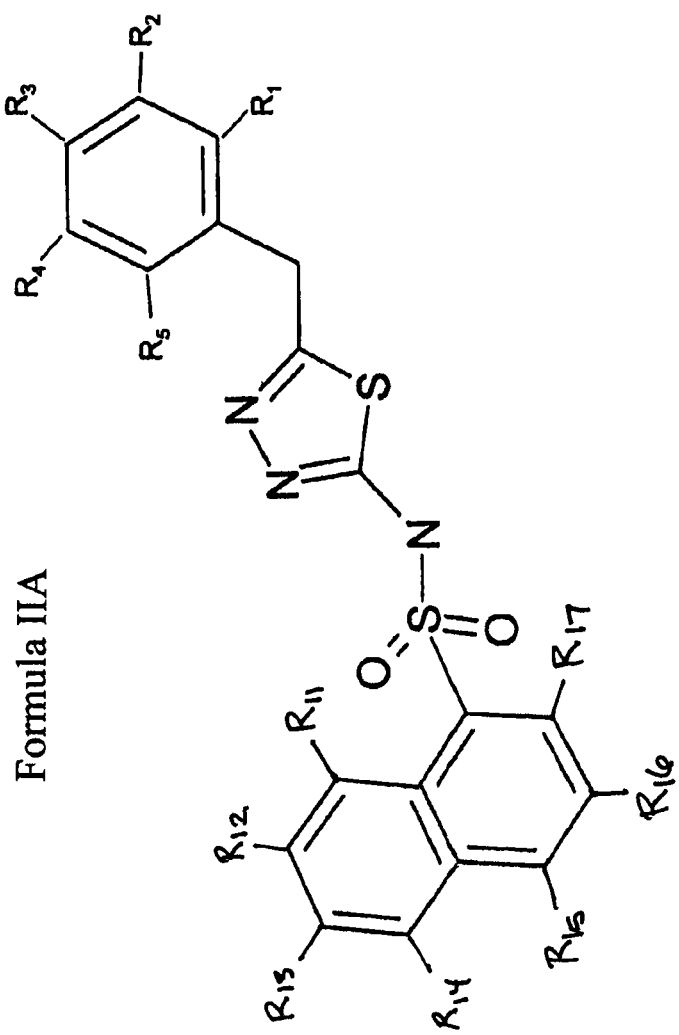
FIG. 7 shows an alternative structure (Formula IIA) of a GGT inhibitor compound used in the methods of the present disclosure.
Figure 8:
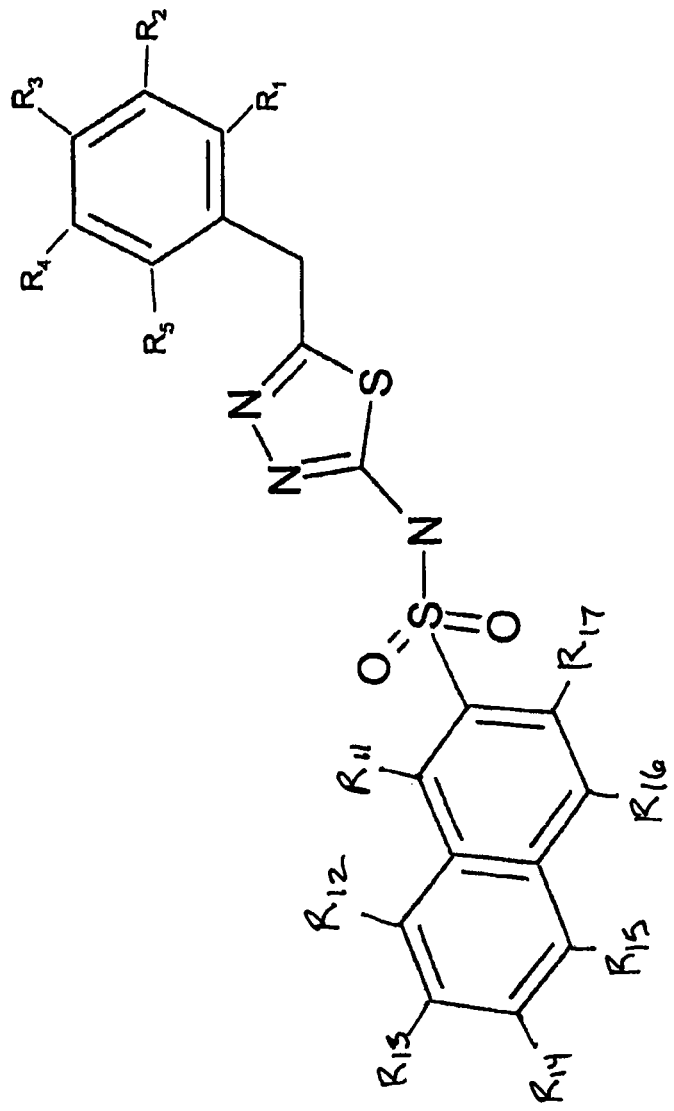
FIG. 8 shows another alternative structure (Formula IIB) of a GGT inhibitor compound used in the methods of the present disclosure.

The GGT inhibitor compounds used in the methods of the present invention, in one embodiment, comprise a class of benzylthiadiazol benzenesulfoniamides represented by the general structure Formula I (FIG. 1), wherein any one or more of $R_1$-$R_{10}$ may be H, Cl, F, Br, I, OH, an alkoxy, or $NO_2$, or, any two or more of $R_1$-$R_{10}$ may be any combination of H, Cl, F, Br, I, OH, an alkoxy, or $NO_2$. Other R groups include carrier groups linked by C, N, or O. The GGT inhibitor compounds used in the methods of the present invention, in other embodiments, comprise a class of benzylthiadiazol naphthylsulfoniamides represented by the general structures Formula IIA (FIG. 7) and Formula IIB (FIG. 8) wherein any one or more of $R_{11}$-$R_{17}$ may be H, Cl, F, Br, I, OH, an alkoxy, or $NO_2$, or, any two or more of $R_{11}$-$R_{17}$ may be any combination of H, Cl, F, Br, I, OH, an alkoxy, or $NO_2$. Other R groups include carrier groups linked by C, N, or O. Further, in the compounds of either of Formula IIA and Formula IIB one or more of adjacent pairs $R_{11}$ and $R_{12}$, $R_{12}$ and $R_{13}$, $R_{13}$ and $R_{14}$, $R_{15}$ and $R_{16}$, and $R_{16}$ and $R_{17}$, may comprise a benzene ring. For example, a benzene ring between the pair $R_{12}$ and $R_{13}$ of Formula IIA would form the naphthylsulfoniamide group into an anthracylsulfoniamide and a benzene ring between the pair $R_{13}$ and $R_{14}$ of Formula IIB would form the naphthylsulfoniamide group into an anthracylsulfoniamide. The invention further comprises use of pharmaceutically acceptable salts of the compounds.

Where used herein, the term "alkoxy" means a lower alkoxy group, methoxy, ethoxy, propoxy (including n-propoxy and iso-propoxy), butoxy (including n-butoxy, tert-butoxy, and sec-butoxy), a pentoxy, a hexoxy, an octoxy, a nonoxy, a decoxy, a undecoxy, a dodecoxy, and heterogeneous alkoxys which comprise, for example, two or more different alkyl groups, in a configuration such as 1,2-dimethylbutoxy. The term "lower alkoxy group" includes straight or branched chain alkoxy group with one to six carbon atoms, such as methoxy, ethoxy, propoxy, isopropoxy, butoxy, tert-butoxy, pentoxy, tert-pentoxy or hexoxy group, and more preferably, methoxy, ethoxy, propoxy or isopropoxy group of one to three carbon atoms.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Any of the inhibitor compounds shown herein may be a component of a pharmaceutical composition which includes a pharmaceutically acceptable carrier such as PBS (phosphate buffered saline). The pharmaceutical composition comprising the inhibitor may further comprise a quantity of glutathione for acting as a substrate for endogenous GGT protein acted on by the GGT inhibitors of the present invention or the glutathione may be provided separately. Also, the GGT inhibitory compounds of the present invention may be connected to a carrier protein such as a serum albumin, for example via carboxymethylcellulose, to enhance the physiological half-life of the inhibitor.

Figure 2A:
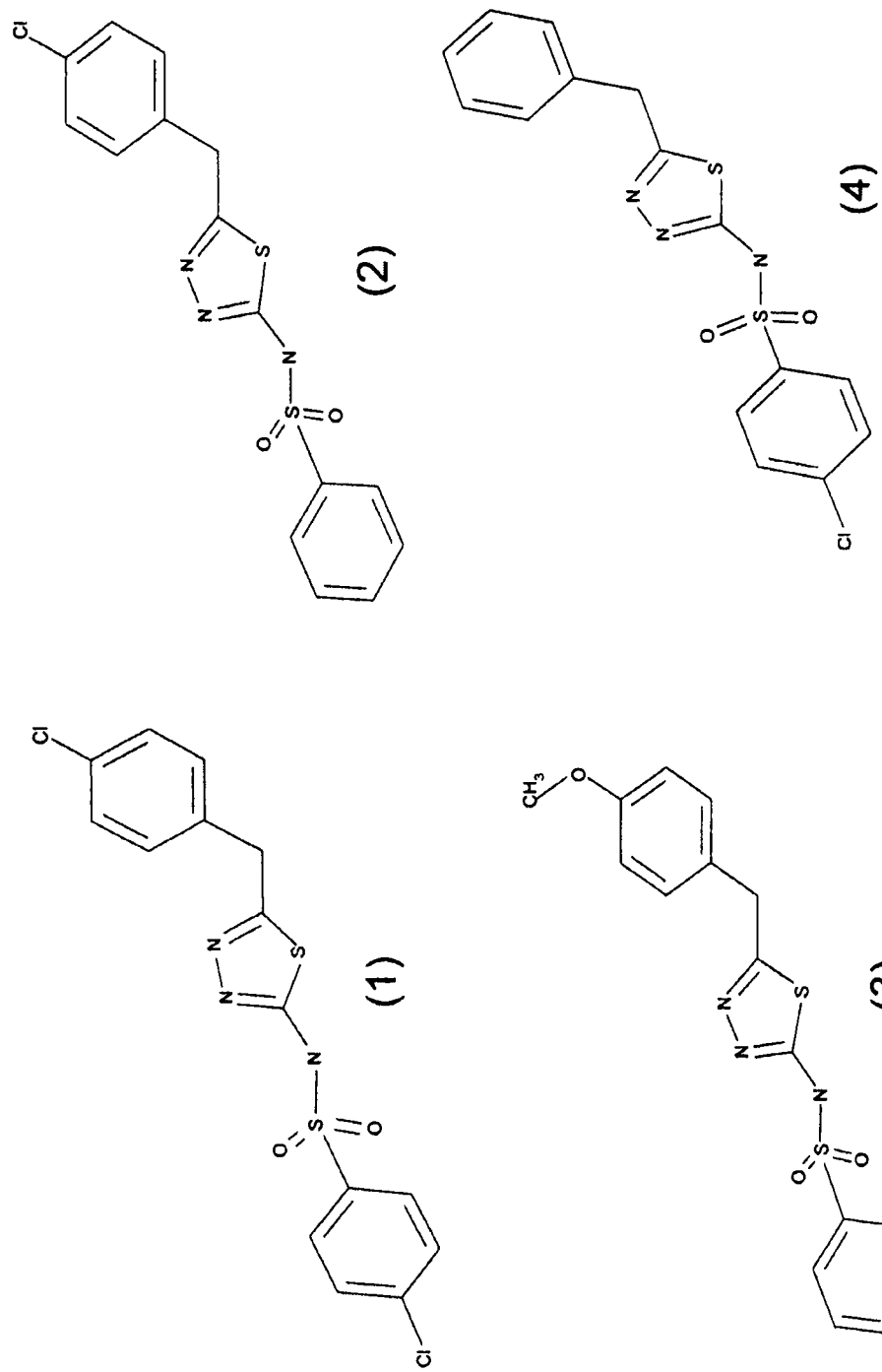
FIG. 2 (A, B) shows examples of nine compounds having varying structures of Formula I, (A) Compounds 1-4, (B) Compounds 5-9.
Figure 2B:
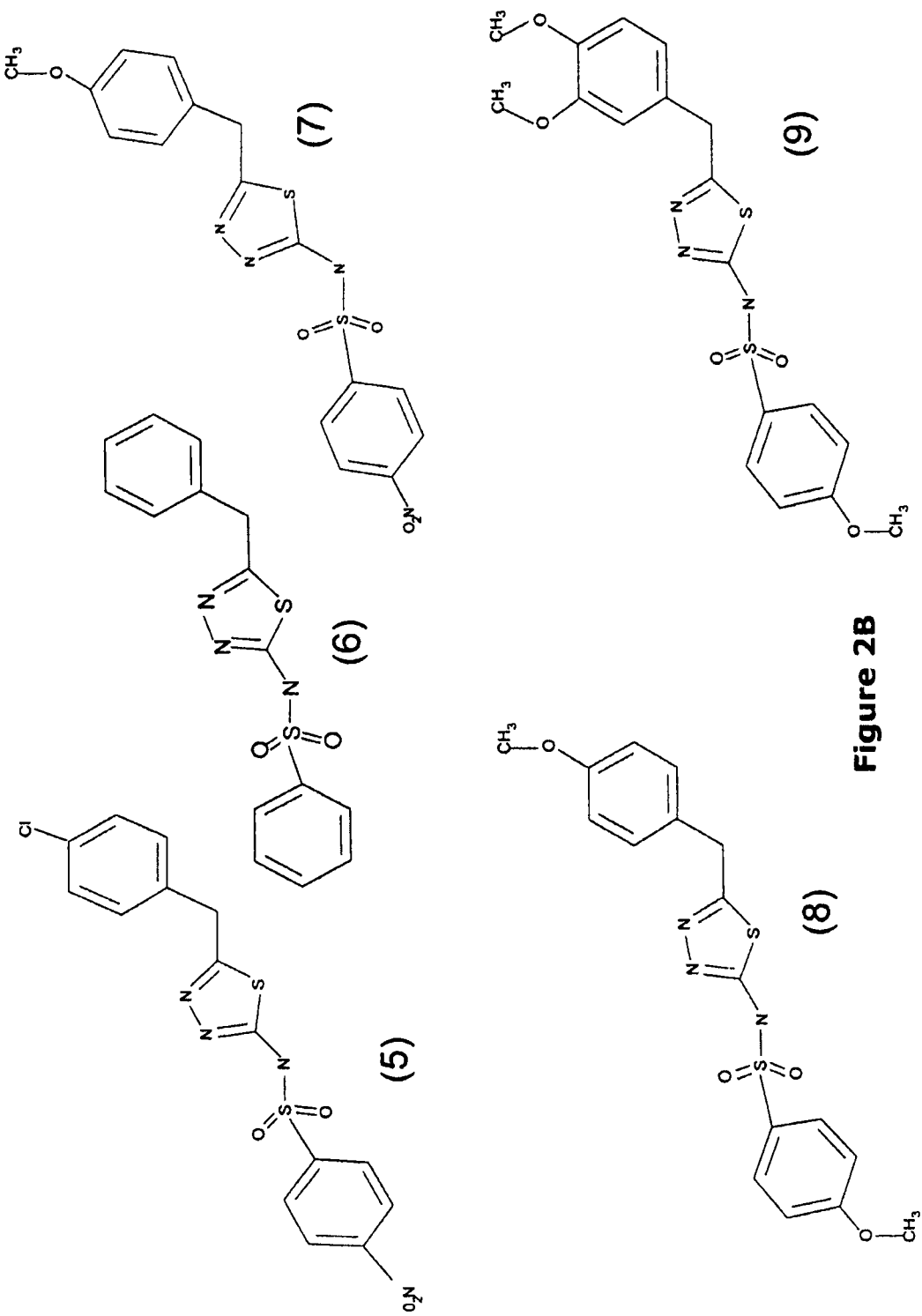

Examples of various embodiments of the compounds represented by Formula I are shown in FIGS. 2A and 2B as compounds (1), (2), (3), (4), (5), (6), (7), (8), and (9). Inhibitory effectiveness of these compounds ((1)-(9)) is discussed below in regard to Table 1.

In one embodiment, the present invention is directed to a method of enhancing the efficacy of an anticancer therapy in a subject having a cancer, comprising administering to the subject a GGT inhibitor of the classes represented by Formula I, IIA, or IIB, or a pharmaceutically acceptable salt thereof, and administering an anticancer therapy (chemotherapy and/or radiation therapy) to the subject, wherein the efficacy of the anticancer therapy is enhanced, for example by enabling use of a higher dosage of the anticancer therapy, and/or by reducing the toxicity of the anticancer therapy.

The methods of the present invention involve administering one or more GGT inhibitory compounds described herein to a person having a susceptible cancer, i.e. a malignant cell population or tumor which expresses extracellular GGT. Compounds used in the present invention are effective on human tumors in vivo as well as on tumor cell lines in vitro. The compounds of the present invention may be particularly useful for the treatment of solid tumors for which relatively few treatments are available. Such tumors include epidermoid and myeloid tumors, acute or chronic, nonsmall cell, and squamous. Specific cancers which are susceptible to treatment by administration of compounds in accordance with the present invention include, but are not limited to, prostate cancer, colon cancer, small cell lung cancer, large cell lung cancer, lung adenocarcinoma, epidermoid lung cancer, melanoma (including amelanotic subtypes), renal cell carcinoma, gastric carcinoma, cancers of the central nervous system, including brain tumors, neuroblastomas, gastric carcinoma, breast cancer, ovarian cancer, testicular cancer, lymphoma and leukemia, esophageal cancer, stomach cancer, liver cancers, cervical cancer, head and neck cancers, adrenal cancer, oral or mucosal cancer, bladder cancer, pancreatic cancer, lymphoma, Hodgkins disease, and sarcomas, hematopoeitic cell cancers such as B cell leukemia/lymphomas, myelomas, T-cell leukemias/lymphomas, small cell leukemias/lymphomas, null cell, sezary, monocytic, myelomonocytic and Hairy cell leukemias. These lymphomas/leukemias can be either acute or chronic. Other cancers may also be susceptible to treatment with the methods of the present invention.

As used herein, the term "carcinomas" refers to lesions that are cancerous. Examples include malignant melanomas, breast cancer, and colon cancer. As used herein, the term "neoplasm" refers to both precancerous and cancerous lesions.

As used herein, the terms "inhibit" or "inhibiting," mean decreasing tumor cell growth rate from the rate that would occur without treatment of the GGT inhibitor and/or causing tumor mass to decrease. Inhibiting also includes causing a complete regression of the tumor. Thus the compounds of the present invention can be either cytostatic or cytotoxic to the tumor cells, when used alone or in combination with other therapies.

As used herein, the terms subject and patient are used interchangeably. Subjects and patients are mammals and in particular are humans.

The invention in one embodiment is directed to a method of treating cancer comprising administering to a patient in need thereof a cancer treatment comprising radiation and/or an effective amount of a chemotherapeutic composition and administering at least one compound of the present invention, with pharmaceutical acceptable additives, diluents, carriers and excipients, and pharmaceutically acceptable salts thereof.

As defined herein, treating cancer (i.e., with an anticancer therapy) in a patient includes achieving, partially or substantially, one or more of the following: arresting the growth or spread of a cancer, reducing the extent of a cancer (e.g., reducing size of a tumor or reducing the number of affected sites) Inhibiting the growth rate of a cancer, and ameliorating or improving a clinical symptom or indicator associated with a cancer (such as tissue or serum components).

The present invention also provides the use of compositions which comprise of one or more of the compounds of the present invention, their derivatives, metabolites, analogues and/or mimic molecules with pharmaceutical acceptable additives, diluents, carriers and excipients and pharmaceutically acceptable salts thereof, for the manufacture of a medicament for a cancerous condition. As noted, the pharmaceutical formulations may be administered in combination (before or simultaneously) with other therapeutic treatments, such as radiation treatment or chemotherapeutic drugs.

In one embodiment, the method, or, pharmaceutical formulation further includes but is not limited to one or more conventional chemotherapeutic agents. Particularly preferred examples of chemotherapeutic agents for use with the GGT inhibitory compounds of the present invention include melphalan, doxorubicin, methotrexate, taxol, vincristine, 6-mercaptopurine, cytosine arabinoside, carboplatin, cisplatin, codetaxel, 5-fluorouracil, cyclophosphamide, and erlotinib. In particular, platinum agents and alkylating agents are preferred. In alternative embodiments, the one or more conventional chemotherapeutic agents may be selected from the group comprising flutamide and luprolide, antiestrogens, such as tamoxifen, antimetabolites and cytotoxic agents, such as daunorubicin, fluorouracil, floxuridine, hexamethylmelamine, interferon alpha, methotrexate, plicamycin, mecaptopurine, thinguanine, adramycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, streptozocin, bleomycin, dactinomycin and idamycin, hormones such as, medroxyprogesterone, ethinyl estradiol, estradiol, leuprolide, megestrol, octreotide, diethylstilbestrol, chlorotrianisene, etoposide, podophyllotoxin, and goserelin, nitrogen mustard derivatives such as, chlorambucil, methlorethamine and thiotepa, steroids such as, betamethasone, and other antineoplastic agents such as live *Mycobacterium bovis*, dicarbazine, asparaginase, leucovoribn, mitotane, vincristine, vinblastine, texotere, and cyclophosphamide. Other chemotherapeutic agents include, but are not limited to, adriamycin, aclarubicin; acodazole hydrochloride; acrqnine; adozelesin; aldesleukin; ambomycin; ametantrone acetate; aminoglutethimide; amsacrine; anastrozole; anthremycin; asperlin; azacitidine; azetepa; azotomycin; abiraterone; acylfulvene; adecypenol; All-TK antagonists; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2: axinastatin 3; azasetron; azatoxin: azatyrosine; batimastat; benzodepa; bicalutamide;

bisantrene hydrochloride; bisnafide dimesylate; bizelesin; bleomycin sulfate; brequinar sodium; bropirimine; busulfan; baccatin III derivatives; balanol; BCR/ABL antagonists; benzochlorins; benzoylslaurosporine; beta lactam derivatives; beta-alethine; betaclamycin B; betulinic acid; bFGF inhibitor; bisaziridinylspermine; bistratene A; breflate; budotitane; buthionine sulfoximine; bromineepiandrosterone; cactinomycin; calusterone; carecemide; carbetimer; carubicin hydrochloride; carzelesin; cedefingol; cirolemycin; cisplatin; cladribine; crisnatol mesylate; calcipotriol; calphostin C; camptothecin derivatives; canarypox IL-2; capecitabine; carboxamide-amino-triazole; carboxyamidotriazole; CaRest M3; CARN 700; cartilage derived inhibitor; casein kinase inhibitors (ICOS); castanospermine; cecropin R4; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacarbazine; daunorubicin hydrochloride; decitabine; dexormaplatin; dezaguanine; dezaguanine mesylate; diaziquone; docetaxel; doxorubicin hydrochloride; droloxifene; droloxifene citrate; dromostanolone propionate; duazomycin; DHEA; dacliximab; dehydrodidemnin B; deslorelin; dexifosfamide; dexrazoxane; dexverapamil; didemnin B; didox; diethylnorspermine; dihydro-5-azacytidine; dihydrotaxol; dioxamycin; diphenyl spiromustine; docosanol; dolasetron; doxifluridine; dronabinol; duocannycin SA; edatrexate; eflornithine hydrochloride; elsamitrucin; enloplatin; enpromate; epipropidine; epirubicin hydrochloride; erbulozole; esorubicin hydrochloride etanidazole; ethiodized oil I 131; etoposide phosphate; etoprine; epiandrosterone; ebselen; ecomustine; edelfosine; edrecolomab; elemene; emitefur; epristeride; estramustine analogue; estrogen agonists; estrogen antagonists; exemestane; fadrozole hydrochloride; fazarabine; fenretinide; floxuridine; fludarabine phosphate; flurocitabine, fosquidone; fostriecin sodium; filgrastim; finasteride; flavopiridol; flezelastine; fluasterone; fluorodaunorunicin hydrochloride; torfenimex; formestane; fotemustine; gemcitabine; gemcitabine hydrochloride; gold Au 198; gadolinium texaphyrin; gallium nitrate; galocitabine; ganirelix; gelatinase inhibitors; glutathione inhibitors, hepsulfam; heregulin; hexamethylene bisacetamide; hypericin; idarubicin hydrochloride; ilmofosine; interferon alfa-2a; interferon alfa-2b; interferon alfa-n1; interferon alfa-n3; interferon beta-Ia; interferon gamma-Ib; iproplatin; irinotecan hydrochloride; ibandronic acid; idoxifene; idramantone; ilomastat; imidazoacridones; imiquimod; immunostimulant peptides; insulin-like growth factor-1 receptor inhibitor; interferon agonists; interleukins; iobenguane; lododoxarubicin; ipomeanol; irinotecan; iroplact; irsogladine; isobengazole; isohomohalicondrin B; itasetron; jasplakinolide; kahalalide F; lanreotide acetate; letrozole; leuprolide acetate; liarozole hydrochloride; lometrexol sodium; losoxantrone hydrochloride; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; linear polyamine analogue; lipophilic disaccharide peptide; lipophilic platinum compounds; lissoclinamide 7; lobaplatin; lombricine; lonidamine; lovastatin; loxoribine; lurtotecan; lutetium texaphyrin; lysofylline; lytic peptides; masoprocol; maytansine; mechlorethamine hydrochloride; megestrol acetate; melengestrol acetate; menogeril; methotrexate sodium; metoprine; meturedepa; mitindomide; mitocarcin; mitocromin; mitogillin; mitomalcin; mitomycin; mitosper; mycophenolic acid; maitansine; mannostatin A; marimastat; maspin; matrilysin inhibitors; matrix metalloproteinase inhibitors; merbarone; meterelin; methioninase; metoclopramide; MIF inhibitor; mifepristone; miltefosine; mirimostim; mismatched double stranded RNA; mitoguazone; mitolactol; mitonafide; mitotoxin fibroblast growth factor-saporin; mofarotene; molgramostim; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; nocodazole; nogalamycin; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; ormaplatin; oxisuran; O6-benzylguanine; octreotide; okicenone; oligonucteotides; onapristone; ondansetron; ondansetron; oracin; oral cytokine inducer; osaterone; oxaliplatin; oxaunomycin; paclitaxel; pegaspargase; pellomycin; pentamustine; peplomycin sulfate; perfosfamide; pipobroman; piposulfan; piroxantrone hydrochloride; plomestane; porfimer sodium; porfiromycin; prednimustine; puromycin; puromycin hydrochloride; pyrazofurin; paclitaxel analogues; paclitaxel derivatives; palauamine; palmitoylrhizoxin; pamidronic acid; panaxytriol; panomifene; parabactin; pazelliptine; peldesine; pentosan polysulfate sodium; pentostatin; pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds: platinum-triamine complex; porfiromycin; propyl bis-acridone; prostaglandin J2; proteasome inhibitors; protein A-based immune modulator; protein kinase C inhibitor; protein kinase C inhibitors; protein tyrosine-phosphatase inhibitors; purine nucleoside phosphorylase inhibitors, purpurins; pyrazoloacridine; pyridoxylated hemoglobin polyoxyethylon conjugate; riboprine; rogletimide; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; safingol hydrochloride; semustine; simtrazene; sparfosate sodium; sparsomycin; spirogermanium hydrochloride; spiromustine; spiroplatin; streptonigrin; strontium chloride Sr 89; saintopin; sarCNU; sarcophytol A; sargramostim; sdi 1 mimetics; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; sulofenur; tallsomycin; taxane; taxoid; tecogalan sodium; tegafur; teloxantrone hydrochloride; temoporfin; teniposide; teroxirone; testolactone; thiamiprine; tiazofurin; tirapazamine; topotecan hydrochloride; toremifene citrate; trestolone acetate; triciribine phosphate; trimetrexate; trimetrexate glucuronate; triptorelin; tubulozole hydrochloride; tallimustine; tamoxifen methiodide; tauromustine; tazarotene; tellurapyrylium; telomerase inhibitors; temozolomide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; titanocene dichloride; topsentin; totipotent stem cell factor; translation inhibitors; tretinoin; triacetyluridine; tropisetron; turosteride; tyrosine kinase inhibitors; tyrphostins; uracil mustard; uredepa; UBC inhibitors; ubenimex; urogenital sinus-derived growth inhibitory factor; urokinase receptor antagonists; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; variolin B; vector system, erythrocyte gene therapy, velaresol; venom; anti-venom; veramine; verdins; vinorelbine; vinxaltine: vitaxin; zeniplatin; zinostatin; zorubicin hydrochloride, zanoterone; zilascorb; 20-epi-1,25 dihydroxyvitamin D3; 5-ethynyluracil; and immunostimulating drugs or therapeutic agents, their metabolites, salts and derivatives of the above.

The invention in one embodiment is directed to a method of suppressing tumor growth in a mammal by first administering to the mammal an amount of a composition which consists of at least one of the GGT inhibitory compounds of the present invention, derivatives, metabolites, analogues and/or mimic molecules, then administering a chemotherapeutic agent or radiation effective to suppress tumor growth in the mammal. The present compound provides enhanced antitumor effect when used with the chemotherapeutic agent or radiation, preferably several hours prior to administering the chemotherapeutic agent or radiation. The compositions can be administered by any efficacious route.

The components (GGT inhibitory compound and chemotherapeutic agents) of any of the pharmaceutical formulations (and/or radiation) disclosed herein can be administered simultaneously (e.g., in a combination formulation), essentially simultaneously (e.g., administration of each compound a few minutes or a few hours apart), or can be administered sequentially, e.g., several days apart, or more than a week apart. For example, a GGT inhibitory compound of the present invention, (and a conventional chemotherapeutic agent) can be administered together, or essentially simultaneously, e.g., administration of each compound a few minutes or a few hours apart, or can be administered sequentially, e.g., several days apart, or more than a week apart. All such variations in administration of the combination therapy are encompassed within the scope of the invention.

The present invention also provides a method for the prophylaxis or treatment of a reversible airways obstruction in a mammal, such as a human, comprising administration of a therapeutically effective amount of a compound of Formula I, IIA, or IIB, or a pharmaceutically acceptable salt, thereof, for the prophylaxis or treatment of a disease associated with reverse airways obstruction such as asthma, chronic obstructive pulmonary disease (COPD), allergic reaction, respiratory tract infection or upper respiratory tract disease.

Compounds of the present invention and their pharmaceutically acceptable salts, also such as have use in the prophylaxis and treatment of clinical conditions associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

The present invention also provides the use of a compound of Formula I, IIA, or IIB, or a pharmaceutically acceptable salt thereof in the use of or manufacture of a medicament for the prophylaxis or treatment of a clinical condition associated with reversible airways obstruction such as asthma, chronic obstructive pulmonary disease (COPD), respiratory tract infection or upper respiratory tract disease.

In one embodiment, the pharmaceutical formulation comprising the compound or compounds described herein has an enteric coating. In one embodiment, the enteric coating is made of a polymer or copolymer. In one embodiment, the polymer or copolymer is selected from the group consisting of poly(lactic-glycolic acid) polyester, cellulose acetate phthalate, hydroxypropyl-methyl cellulose phthalate poly (butyl methacrylate), (2-dimethyl aminoethyl) methacrylate, and methyl methacrylate.

The pharmaceutical formulation according to the present invention can be administered to a patient in any of a wide range of routes. Thus, with regard to the types of formulations in which the active compounds according to the present invention can be administered, as well as any additives can be included with the active compounds in the formulations, and the possible routes of administration, it is well known to those of ordinary skill in the art that such formulations can be provided in a wide variety of types, and it is within the skill of the ordinary artisans to select a specific formulation and route of administration and then test suitability for use. By way of example but not limitation, suitable routes include enteric, parenteral, topical, oral, rectal, nasal or vaginal routes. Parenteral routes include subcutaneous, intramuscular, intravenous, intraperitoneal, intradermal and sublingual administration. Also, compositions may be implanted into a patient or injected using a drug delivery system.

The pharmaceutical formulation according to the present invention may be administered locally or systemically. By systemic administration means any mode or route of administration that results in effective amounts of active ingredient appearing in the blood or at a site remote from the route of administration of the active ingredient.

Further, the pharmaceutical formulation according to the present invention may be administered intermittently. The advantage of this is that it allows the patient to suspend therapy for periods without the worry of inactivity of the drug resulting from the development of resistant cells.

The pharmaceutical formulation according to the invention may be formulated for enteral, parenteral or topical administration. Indeed all three types of formulations may be used simultaneously to achieve systemic administration of the active ingredient.

Compounds useful in the methods of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the coated compound can be pressed into a tablet, pill, or granule, and the tablet, pill or granules for administration to the patient. Preferred enteric coatings include those that dissolve or disintegrate at colonic pH such as shellac or Eudraget S. Additional pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of the present invention, excipients such as cocoa butter or a suppository wax.

Suitable injectable solutions include intravenous, subcutaneous, and intramuscular injectable solutions. Examples of injectable forms include solutions, suspensions and emulsions. Typically the compound(s) is injected in association with a pharmaceutical carrier such as normal saline, Ringers solution, dextrose solution and other aqueous carriers known in the art. Appropriate non-aqueous carriers may also be used and examples include cyclodextrin, preferably hydroxypropyl beta cyclodextrin, mixed oils (vitamin E oil), polyethylene glycol and ethyl oleate. A preferred carrier is cyclodextrin in water. Frequently, it is desirable to include additives in the carrier such as buffers and preservatives or other substances to enhance isotonicity and chemical stability.

When prepared as a solid composition for oral administration, the compound of the present invention may be formed in any suitable dosage form including tablet, pill, powder, and granule. In such a solid composition, one or more active substances are mixed with at least one of inactive diluent, dispersant, and adsorbent, such as lactose, mannitol, glucose, hydroxypropylcellulose, microcrystalline cellulose, starch, polyvinyl pyrrolidone, magnesium aluminate metasilicate, or silicic acid anhydride powder. In addition, the composition may be mixed with additives other than diluents based on common manner in the art.

When prepared as tablets or pills, they may be coated, if necessary, with one or more films of gastric or enteric coating substance, such as saccharose, gelatin, hydroxypropylcellulose or hydroxymethylcellulose phthalate. Further, they may be capsuled with substance, such as gelatin or ethyl cellulose.

When prepared as a liquid composition for oral administration, the compound of the present invention may be formed in any suitable dosage form including pharmaceutically acceptable emulsion, resolvent, suspension, syrup, elixir or the like. A suitable diluent may include purified water, ethanol, vegetable oil, or emulsifier. Further, this composition may be mixed with an auxiliary agent other than diluent, such as humectant, suspension, sweetening agent, flavor agent, fragrance agent, or antiseptic agent.

When prepared as injection for parenteral administration, axenic aqueous or non-aqueous solution agents, solubilizing agents, suspensions or emulsifiers are used. Aqueous solution agent, solubilizing agents or solution agent may include water for injection, distilled water for injection, physiological saline; cyclodextorin and derivatives thereof, organic amines, such as triethanolamine, diethanolamine, monoethanolamine, and triethylamine, inorganic alkali solution or the like.

For example, propylene glycol, polyethylene glycol, vegetable oils such as olive oil, or alcohols such as ethanol, may be used for preparing as the water-soluble solution. Further, a surface-active agent (mixed micelle formation), such as polyoxyethylene hydrogenated castor oil or sucrose fatty acid ester, or lecithin or hydrogenated lecithin (liposome formation) may be used for preparing as the solubilizing agent. Further, the compound of the present invention may be prepared as an emulsion drug comprising water insoluble resolvent such as vegetable oils, and lecithin, polyoxyethylene hydrogenated castor oil or polyoxyethylene polyoxypropylene glycol.

Alternately, for parenteral administration, the composition may be formed in lotion, liniment such as ointment, suppository, or pessary, which contains one or more active substances and is prepared by well-known processes.

The composition can also be administered topically. Suitable formulations for topical administration include creams, gels, jellies, mucliages, pastes and ointments. The compounds may be formulated for transdermal administration, for example in the form of transdermal patches so as to achieve systemic administration. The composition may also be administered in the form of an implant. The composition may also be administered in the form of an infusion solution or as a nasal or bronchial inhalation, aerosol or spray. In another embodiment, the composition is incorporated in a pharmaceutically acceptable carrier, diluents, vehicles and the like for systemic administration by feeding. An example of such a carrier is cyclodextrin (e.g., $\alpha$-cyclodextrin, $\beta$-hydroxypropylcyclodextrin or $\gamma$-cyclodextrin).

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve cancer-therapeutic activity in accordance with the desired method of administration. The selected dosage level therefore depends upon the nature of the active compound administered, the route of administration, the desired duration of treatment, individual needs and other factors. If desired, the unit dosage may be such that the daily requirement for active compound is in one dose, or divided among multiple doses for administration, e.g., two to four times per day.

The dosage of the compound represented by the general Formula I, IIA, or IIB, or the salt or prodrug thereof is varied depending on age, weight, symptoms, therapeutic effects, administration route, treatment time and the like. In one embodiment the compound may be administered orally or parenterally at an amount in the range of, but not limited to, 0.01 mg to 1 g per adult and one to several times a day. With regard to dosage and duration of treatment according to any aspect of the present invention, it is recognized that the ability of an artisan skilled in pharmaceutical administration of drugs to determine suitable dosages depending on many interrelated factors is well known, and skilled artisans are readily able to monitor patients to determine whether treatment should be started, continued, discontinued or resumed at any given time. For example, dosages of the compounds are suitably determined depending on the symptoms of the individual subject. The weight, age and sex of the subject and the like are also taken into consideration. The amount of the compound to be incorporated into the pharmaceutical composition of the invention varies with dosage route, solubility of the compound, administration route, administration scheme and the like. An effective amount for a particular patient may vary depending on factors such as the condition being treated, the overall health of the patient and the method, route and dose of administration. The clinician using parameters known in the art makes determination of the appropriate dose. Generally, the dose begins with an amount somewhat less than the optimum dose and it is increased by small increments thereafter until the desired or optimum is effect is achieved. Suitable dosages can be determined by further taking into account relevant disclosure in the known art. In one embodiment, the unit dose comprises (but is not limited to) 5-1000 mg of active ingredient consisting of at least one compound of the present invention.

The amount of a compound of Formula I, IIA, or IIB, or a pharmaceutically acceptable salt thereof which is required to achieve a therapeutic effect in the treatment of a respiratory condition will, of course, vary with the particular compound, the route of administration, the subject under treatment, and the particular disorder or disease being treated. The compounds of the invention may be administered by inhalation at a dose (such as, but not limited to) of from 0.0005 mg to 100 mg.

While it is possible for the compound of Formula I, IIA, or IIB, or a pharmaceutically acceptable salt thereof to be administered alone, it is preferable to present it as a pharmaceutical formulation. Accordingly, the present invention further provides a pharmaceutical formulation comprising a compound of Formula I, IIA, or IIB, or a pharmaceutically acceptable salt thereof, and a pharmaceutically acceptable carrier or excipient, and optionally one or more other therapeutic ingredients used for the treatment of respiratory conditions such as asthma.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. In one embodiment each capsule or cartridge may generally contain between 20 μg-10 mg of the compound of Formula I, IIA, or IIB optionally in combination with another therapeutically active ingredient. Alternatively, the compound of the invention may be presented without excipients. Packaging of the formulation may be suitable for unit dose or multi-dose delivery.

Spray compositions for topical delivery to the lung by inhalation may for example be formulated as aqueous solutions or suspensions or as aerosols delivered from pressurized packs, such as a metered dose inhaler, with the use of a suitable liquefied propellant. Aerosol compositions suitable for inhalation can be either a suspension or a solution and generally contain the compound of Formula I, IIA, or IIB optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurized formulations will generally be retained in a canister (eg an aluminum canister) closed with a valve (e.g., a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The compounds and pharmaceutical formulations of the present invention for use in treating respiratory conditions may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of Formula I, IIA, or IIB, or a pharmaceutically acceptable salt thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of Formula I, IIA, or IIB, or a pharmaceutically acceptable salt thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimize the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hy-droxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1, 4-diene-17β-carbothioic acid S-(2-oxo-tetrahydro-furan-3 S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred cortico steroids include fluticasone propionate, 6α,9α-difluoro-11β-hydroxy-16α-methyl-17α-[(-4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hy-droxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hy-droxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, β2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

The present invention is also directed to compositions comprising at least one compound of Formula I, IIA, or IIB of the present invention and another compound acting as a prodrug compound analogous to a chemotherapeutic compound disclosed herein. Such pending compounds are generally themselves inactive or low in activity, but are converted into active compounds. Thus, for example, pro-drugs such as the methyl ester of any acid functionality, which is not active per se or has very low activity could be hydrolyzed, either uncatalytically or catalytically with an enzyme such as an esterase to an active compound. Such pro-drug compounds could well be the preferred therapeutic form of the present compounds. These analogous prodrugs can be produced from active compounds based on procedures and factors that are well known to one of ordinary skill in the art. Accordingly as used in the present application, "pro-drug analogue" means "a chemical which is relatively non-toxic and pharmacologically inert but which can be transformed in vivo to a pharmacologically active drug". More specifically it means a derivative, metabolite or analogue of the compounds of the present invention which have low or no ability as anti-neoplastic agents until converted in the body to a derivative, metabolite or analogue with such ability or abilities. Such pro-drugs should have favorable properties such as enhanced absorption, water solubility, lower toxicity, or better targeting to the tumor cell (such as by reason of greater affinity to the tumor cell or a larger quantity of activating enzyme in the tumor cell as opposed to a normal cell so that larger concentrations of the active compound are produced in the tumor cell). Examples of such compounds are esters, such as methyl, ethyl, phenyl, N,N-dimethylaminoethyl, acyl derivatives such as benzoyl, p-N, N-dimethylaminobenzoyl, N,N-dimethylaminoglycyl, peptide derivatives such as γ-glutamyl, glycyl, and D-Val-Leu-Lys.

The compositions containing the active compounds or pro-drugs of the present invention can be formulated so as to be specifically targeted to tumors. The compounds can be attached to the reagent that is capable of binding a tumor-associated antigen. For example, the compounds of the present invention could be covalently attached to a monoclonal antibody such as directed to a tumor-associated antigen. The antigen may be located on a tumor or in the tumor cell area. Such linkages can be made through peptide bond formation with amino groups of an antibody. Suitable reagents include polyclonal and monoclonal antibodies. Accordingly, the present invention also provides a method comprising treating cancer (i.e. inhibiting tumor cell growth) by administering a pharmaceutical composition comprising at least one of the compounds of the present invention and a reagent (i.e., monoclonal or polyclonal antibody or other targeting agent) which is capable of binding to a tumor-associated antigen.

Alternatively, the compounds of the present invention could be attached to or incorporated into liposomes or carbohydrate vehicles, which are known to be useful far targeting anti-cancer drugs. Preferably the liposomes or carbohydrate vehicles can be specifically targeted to tumors by covalently attaching a monoclonal antibody directed to a tumor-associated antigen.

The present invention is exemplified in terms of in vitro and in vivo activity against various neoplastic cell lines. The test cell lines employed in the in vitro assays are well recognized and accepted as models for anti-tumor activity in animals. The term animals as used herein includes, but is not limited to, mice, rats, domesticated animals such as but is not limited to, cats, dogs, and other animals but is not limited to, cattle, sheep, pigs, horses, and primates such as but not limited to, monkeys, humans and more generally mammals.

As used herein, pharmaceutically acceptable refers to those properties and/or substances, which are acceptable to the patient from a pharmacological/toxicological point of view including bioavailability and patient acceptance or to the manufacturing chemist from a physical-chemical point of view regarding composition, formulation, stability and isolatability.

For the purpose of describing the present invention, terms used herein will be defined generally as follows.

The terms "comprise, comprised and comprising" and the terms "include, included and including" are used interchangeably in this specification and are to be afforded the widest interpretation.

As used herein, the terms "cytotoxic agent", "chemotherapeutic agent", "anticancer agent", and "antitumor agent" are used interchangeably herein and refer to agents that have the property of inhibiting the growth or proliferation (e.g., a cytostatic agent), or inducing the killing, of hyperproliferative cells.

As used herein, a "therapeutically effective amount" the GGT inhibitor or chemotherapeutic agent of the invention refers to an amount of a compound that is effective, upon single- or multiple-dose administration to the subject, e.g., a patient, at enhancing the inhibition of the growth or proliferation, or inducing the killing, of hyperproliferative cells, e.g., cancer cells by a chemotherapeutic compound or by radiation treatment. The term, for example, "therapeutically effective amount" refers to an amount of a GGT inhibitory compound of the invention that is administered, e.g., coadministered, (i.e., sequentially or concomitantly) with one or more cytotoxic agents such that the GGT inhibitory compound and the cytotoxic agent, are effective, upon single- or multiple-dose administration to the subject, e.g., a patient, at inhibiting the growth or proliferation, or inducing the killing, of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

As used herein, "chemosensitization" and "chemosensitizing effect" are used interchangeably and refer to the enhancement of radiation or chemotherapy efficacy by the compound. "Chemosensitizer" refers to the agent, that enhances the efficacy of another agent, such as the cytotoxic agent or radiation.

The term "a drug or compound for overcoming a resistance to an anticancer drug or an anticancer-drug-resistance overcoming drug" or "a pharmaceutical composition for overcoming a resistance to an anticancer drug or an anticancer-drug-resistance overcoming pharmaceutical-composition" refers to a drug which has no carcinostatic activity itself but has a function of reducing a resistance of cancer cells to an anticancer drug. In other words, it means a drug having a function for increase a sensitivity to an anticancer drug of cancer cells having an acquired resistance to the anticancer drug. In this case, the increase of the sensitivity means not only to increase an effect of an anticancer drug to anticancer-drug resistant cells in a higher level than that to anticancer-drug sensitive cells but also to increase the effect of the anticancer drug to the anticancer-drug resistant cells in approximately the same level as that to the anticancer-drug sensitive cells. Further, another term equivalent to "overcoming a resistance" may include "restraining or inhibiting a resistance", "releasing resistance", "releasing tolerance" or "increasing or enhancing a sensitivity".

The term "a drug or compound for enhancing a effect of an anticancer drug or an anticancer-drug-effect enhancing drug" or "a pharmaceutical composition for enhancing an effect of an anticancer drug or an anticancer-drug effect enhancing pharmaceutical-composition" refers to a drug which has no carcinostatic activity itself but enhances an activity of an anticancer drug or therapy, i.e., an carcinostatic effect of an anticancer drug itself, by administering it together with or apart from the anticancer drug. In this case, the term "enhancing or increasing" means not only to increase an effect level of an anticancer drug to anticancer-drug resistant cells in an equal to or higher than that to anticancer-drug sensitive cells but also to increase a sensitivity of cancer cells, which have not acquired any resistance, to the anticancer drug.

Therefore, by using the anticancer-drug-resistance overcoming drug or the anticancer-drug-effect enhancing drug according to the present invention, a sensitivity of cancer cells having an acquired resistance to an anticancer drug can be increased, and thereby the dosage of the anticancer drug can be reduced or the intervals of administration of the anticancer drug can be extended.

The term "a method for overcoming a resistance to an anticancer drug" means a method for reducing a resistance of cancer cells to an anticancer drug, i.e. a method for increasing a sensitivity of cancer cells, which have acquired a resistance to an anticancer drug, to the anticancer drug.

The term "a method for enhancing or increasing an effect of an anticancer drug" means a method for enhancing or increasing an activity of an anticancer drug, in other word, a method for enhancing or increasing an carcinostatic effect of an anticancer drug itself.

The anticancer-drug-resistance overcoming drug or the anticancer-drug-effect enhancing drug of the present invention may be used by administering together with an anticancer drug in treating cancer (malignant tumor), such as lung cancer (non-small cell lung cancer, small cell lung cancer), large intestine cancer (rectum cancer, colon cancer), small intestine cancer, gastric cancer, esophageal cancer, hepatic cancer, pancreatic cancer, malignant melanoma, renal cancer, bladder cancer, uterine cancer (cervical cancer, corpus uteri cancer), ovarian cancer, mammary cancer, osteosarcoma, malignant lymphoma, prostate cancer, leukemia (acute leukemia, chronic leukemia), myeloma, neuroblastoma, head and neck cancer, skin cancer, and orchidoncus, in mammals including human.

The term "administrating together with" in the present invention means administering two kinds of drugs simultaneously, continuously or at intervals. The two kinds of drugs may be administered as a mixture or as separate drugs. When administering as separate drugs, each administering route may be or may be not the same.

In one aspect, the invention features the use of a GGT inhibitory compound of the invention as a chemosensitizer, in combination with at least one other chemotherapeutic agent or radiation dosage. In a preferred embodiment, the compound is co-administered with the chemotherapeutic agent, to a subject. In a preferred embodiment, the compound is coadministered with repeated dosages of the same, or a different chemotherapeutic agent, to a subject.

In a preferred embodiment, the GGT inhibitory compound enhances the efficacy of the chemotherapeutic agent, e.g., a cytotoxic agent or radiation dosage, relative to the effect of the cytotoxic agent or radiation dosage in the absence of the compound.

As noted elsewhere herein, the compound of the invention is administered in combination with at least one cytotoxic agent. The term "in combination" in this context means that the agents are given substantially contemporaneously, either simultaneously or sequentially (before or after). If given sequentially, at the onset of administration of the second compound, the first of the two compounds is preferably still detectable at effective concentrations at the site where treatment effect is desired.

For example, the compound is used in combination therapy with conventional cancer chemotherapeutics or treatments. Conventional treatment regimens for tumors include radiation, antitumor agents, interferons, interleukins, tumor necrosis factors, or a combination of two or more of these agents, as well as other chemotherapeutic (cytotoxic) agents described herein.

In an alternative embodiment, the compounds of the invention are used as pharmaceutical compositions for the treatment of degenerative diseases. In particular it pertains to the treatment of chronic renal or inner ear conditions or injuries which are reactive oxygen species (ROS) induced. Degenerative diseases are considered to be diseases which are linked to chronic disorders and/or chronic physiological damages in the human or animal body. Besides degenerative diseases of, inter alia, the central nervous system, chronic disorders of the kidneys or the liver may lead to degeneration of the corresponding tissues. For example renal diseases, or inner ear degenerative diseases are frequent pathological conditions for which few treatments are available.

In particular, glomerulosclerosis and other renal diseases are a frequent complication of many chronic conditions including diabetes, wherein an excess of reactive oxygen species (ROS) is thought to play a crucial role desired specificity, considering, for instance, the particular oxygen species to be scavenged as well as its site of action. It would be advantageous to inhibit specifically the enzymatic activity that generates the particular ROS responsible for the tissue damage. Recently, reaction conditions have been defined in vitro, in which ROS are formed as a consequence of the action of the enzyme GGT.

Thus, the present invention thus also relates to the use of GGT inhibitors described herein for the preparation of pharmaceutical compositions for the treatment of a degenerative disease.

It has been found that overexpression of the enzyme GGT is a source of damaging ROS in the kidney and other cells, in particular of cells of the inner ear. Thus, the inhibition of GGT (systemic or local) will lead to means and methods for successfully and effectively preventing the progress of the chronic tissue damage imposed by elevated ROS levels in kidney and inner ear.

Particularly preferred examples of chronic renal diseases contemplated for treatment herein are focal and/or segmental glomerulosclerosis, minimal change nephrosis, inflammatory and/or autoimmune glomerulopathies and diabetic nephropathy.

In the context of the invention, examples of inner ear injuries contemplated for treatment herein are sensineural deafness induced by age, physiological status, metabolical status and/or drugs, one example of an inner ear degenerative condition treatable according to the invention is otosclerosis.

Thus, in one embodiment, the invention is a method of treating a patient for a degenerative disease or condition comprising a chronic renal disease, cardiovascular disease or an inner ear degenerative condition or injury, comprising administering to the patient a composition comprising the GGT inhibitory compounds described herein. The chronic renal disease may be focal glomerulosclerosis, segmental glomerulosclerosis, minimal change nephrosis, inflammatory glomerulopathies, diabetic nephropathy and autoimmuno glomerulopathies. The degenerative disease or condition may be ROS induced. The inner ear injury or condition may be sensineural deafness induced by age, physiological status, metabolic status or drugs, or otosclerosis.

The invention now being generally described, it will be more readily understood by reference to the following examples, which are included merely for purposes of illustration of certain aspects and embodiments of the present invention, and are not intended to limit the invention. Without further elaboration, it is believed that one skilled in the art can, using the preceding description, practice the present invention to its fullest extent. The following detailed examples and methods describe how to make and use the various compounds of this invention and are to be construed, as noted above, as merely illustrative, and not limitations of the preceding disclosure in any way whatsoever. Those skilled in the art will promptly recognize appropriate variations from the procedures.

EXPERIMENTAL

Methods

Screening Assay

An assay method was developed to screen for inhibitors of GGT. The assays were conducted in 96-well plates. The final volume in each well was 100 µL. The assay buffer contained: 100 mM $Na_2HPO_4$ pH 7.4, with 3.2 mM KCl, 1.8 mM $KH_2PO_4$, and 27.5 mM NaCl. Each reaction contained 1 mM L-glutamic acid γ-4-nitroanilide HCl (GpNA) and 40 mM glycyl-glycine (Gly-Gly)(19). GGT is expressed on the cell surface and the assay was initiated by addition of $10^4$ 786-O cells (ATCC CRL-1932, a GGT-positive human renal cell adenocarcinoma line). Formation of the product, p-nitroaniline at 37° C., was monitored continuously at $OD_{405}$ by a Bio-Rad Model 680 Microplate Reader with Microplate Manager 5.2 software (Bio-Rad). One unit of GGT activity was defined as the amount of GGT which released one µmole of p-nitroaniline/min at 37° C.

Compounds for testing were placed in the 96-well plates with 0.25 µmoles test compound per well. Stock solutions were prepared by the addition of 25 µL dimethyl sulfoxide (DMSO) per well. For each test compound, 5 µL was added to the assay mixture, resulting in a final concentration of 500 µM. Glutathione is a competitive inhibitor of the GpNA substrate, and wells containing 400 µM oxidized glutathione were included on each 96-well plate as a positive control. Compounds which inhibited GGT activity to the same extent or greater than glutathione were scored as positive hits. The positive hits were retested at several concentrations for inhibition of GGT activity.

Enzyme Isolation

GGT was isolated from human kidney (National Disease Research Interchange, Philadelphia, Pa.), male Sprague-Dawley rat kidney and female Balb/c mouse kidney. Tissue was homogenized in 4 volumes of 25 mM Tris pH 7.5, containing 0.33 M sucrose, 0.2 mM EDTA, 1 µM leupeptin and 1.4 µg/ml aprotinin. A 9000 g supernatant was spun at 100,000 g for 1 h. The microsomal pellet was homogenized in 25 mM Tris pH 7.35, 0.5% Triton X-100, 1 µM leupeptin, 1.4 µg/ml aprotinin then centrifuged again at 100,000 g for 1 h. The supernatant was assayed for GGT activity, aliquoted, and stored at −80° C. until further use. All solutions were maintained at 4° C. throughout the isolation. The specific activities of GGT were 3.4, 7.4, and 1.5 units/mg protein for human, rat, and mouse preparations, respectively. Prior to use in the GGT assay, the enzyme was diluted in phosphate-buffered saline (PBS) containing 0.025% Triton X-100 and 0.19 m Units of enzyme were used per assay unless otherwise indicated.

Cloning of Human GGT and Expression in *Pichia pastoris*

The soluble domain of human GGT (amino acids 28-569) was amplified by PCR. The forward primer introduced a EcoRI restriction site and a TEV protease-cleavable N-terminal His6 tag, while the reverse primer introduced a NotI restriction site after the stop codon of genomic GGT. The PCR product was digested with EcoRI and Not I and inserted into the corresponding sites of pPICZαA (Invitrogen), generating plasmid pMW-102. This construct was amplified in *E. coli* DH5α cells. The fidelity of the recombinant ORF was verified by sequencing (Oklahoma Medical Research Foundation's DNA Sequencing Core Facility, Oklahoma City, Okla.). The SacI-linearized plasmid, pMW-102, was purified and transformed into wild-type *Pichia pastoris* strain X-33, selected and induced as recommended by Invitrogen. Secreted, recombinant, His6-tagged, human GGT was collected from the media with a Ni-NTA column. The hexahistidine tag was cleaved with His6-tagged TEV protease. TEV protease and the cleaved histidine tag were separated from human GGT by collecting the flow-through from a second Ni-NTA column purification. The specific activity of the purified enzyme was 397.8 units/mg. Prior to use in the GGT assay, the enzyme was diluted in PBS and 2.8 mUnits of enzyme were used per assay.

Kinetic Studies

The assay buffer contained: 100 mM $Na_2HPO_4$ pH 7.4, with 3.2 mM KCl, 1.8 mM $KH_2PO_4$, and 27.5 mM NaCl. The concentrations of the substrate GpNA and the acceptor Gly-Gly were varied as indicated. Purified GGT was added to initiate the assay. The reaction was monitored as described for the high throughput screening.

Cytotoxicity Assays

786-O (ATCC CRL-1932), a human renal cell adenocarcinoma line, was plated in DMEM supplemented with 5% FBS and penicillin/streptomycin (50 U/mL, 50 ug/mL) at $10^3$ cells per well in 96-well plates. The next day the medium was changed to fresh DMEM containing FBS, antibiotics and the test compound. Equivalent concentrations of DMSO were added to control wells. Cell viability was determined by the MTT assay 72 hr after the addition of the test compound (20).

Cell Lines

LLC-$PK_1$ (ATCC CRL 1392), a pig kidney cell line, NRK-52E (ATCC CRL-1571), a normal rat kidney cell line, LLC-MK2 (ATCC CCL-7), a normal kidney monkey cell line, and 786-O cells were grown in complete Dulbecco's Modified Eagle's Medium (DMEM) supplemented with 5% FBS (Hyclone, Logan, Utah), and penicillin/streptomycin (50 U/mL, 50 µg/mL) (Invitrogen, Carlsbad, Calif.). NIH/3T3 cells transfected with cDNA encoding human GGT were described previously and were grown in DMEM/F12 containing 200 µg/mL of G418 (6). HK-2 (ATCC CRL-2190), a human cell line derived from immortalized normal proximal tubule cells, were grown in keratinocyte serum-free media (K-SFM) from ATCC (Manassas, Va.). The cells were trypsinized off the plates and suspended in PBS for the GGT assay.

Glutathione Degradation

An incubation mixture contained 1 mM glutathione, 40 mM glycyl-glycine, and inhibitor in the GGT assay buffer.

Reactions were initiated with the addition of 1.9 mU of GGT and incubated at 37° C. The final volume of the reaction was 100 µL. Aliquots of the reaction mixture were removed at the specified time points, immediately acidified with an equal volume of cold 4.31% 5-sulfosalicylic acid, and maintained at 4° C. until glutathione concentration was determined by the method of Tietze (21).

Data Analysis

Initial velocity data were first analyzed graphically using double-reciprocal plots of initial velocities versus substrate concentration and suitable secondary plots. Data were then fitted using the appropriate equation and the Marquardt-Levenberg algorithm supplied with the EnzFitter program from BIOSOFT, Cambridge, U.K. Kinetic parameters and their corresponding standard errors were estimated using a simple weighting method.

Data for competitive and uncompetitive inhibition were fitted using Equations 1 and 2.

$$v = \frac{VA}{K_a(1+K_{is}) + A} \quad [1]$$

$$v = \frac{VA}{K_a + A(1+K_{ii})} \quad [2]$$

In Equations 1 and 2, v and V are the measured initial rate and maximum rate, respectively, $K_a$ is the Michaelis constant for the varied substrate, and $K_{is}$ and $K_{ii}$ are slope and intercept inhibition constants.

The $LD_{50}$ and 95% confidence intervals of the test compounds in cell lines were calculated with a Prism log (inhibitor) vs normalized response (variable slope) curve fit (Prism, GraphPad Software Inc., San Diego, Calif.). A two-tailed t-test was used to detect significant differences between OU749 inhibition of human GGT and inhibition of GGT from other species.

Results

Screening for Inhibitors of GGT

Figure 3:
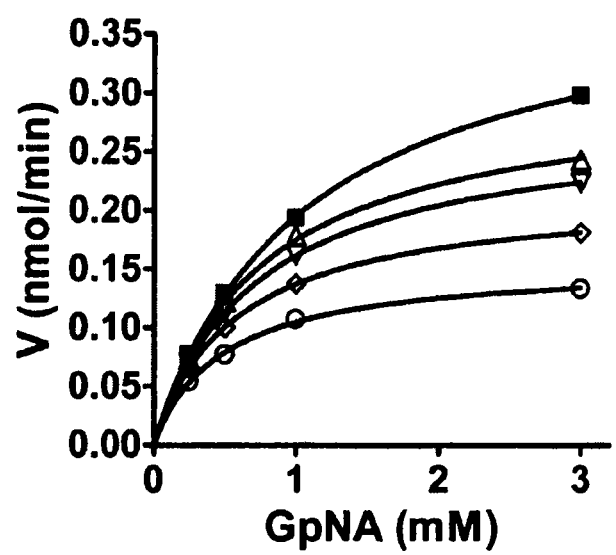
FIG. 3. Inhibition of GGT by compound 3. The substrate velocity curves for the inhibition of human kidney GGT by 0 (■), 15.2 µM (Δ), 31.3 µM (∇), 62.5 µM (◊), 125 µM (○) of compound 3 in the presence of 40 mM glycylglycine are shown. Data shown are the average of triplicate values±S.D. (for many points the error bars are smaller than the symbol).

An initial screening of a library of compounds identified 16 hits. When retested, 12 of the compounds were only weak inhibitors and not pursued further. Three of the four remaining compounds were derivatives of isoindole-1,3-dione. Additional evaluation of this group of compounds revealed low solubility in aqueous solution and severe toxicity in a cell based assay. These compounds were not pursued further. The last of the initial 16 hits was previously unknown as an inhibitor of GGT. The inhibitor, N-[5-(4-methoxybenzyl)-1,3,4-thiadiazol-2-yl]benzenesulfonamide, is shown as compound (3) in FIG. 2A. The structure of compound 3 reveals that it is not a glutamine analogue. It inhibited GGT isolated from human kidney in a dose-dependent manner (FIG. 3).

Kinetic Analysis of Inhibition of GGT by Compound 3.

To determine the mechanism of compound 3 inhibition of human kidney GGT, inhibition patterns were obtained varying each of the substrates with the second maintained at a fixed concentration. With GpNA (the first substrate) varied, glygly was maintained at 40 mM ($K_{glygly}$ is 11.4±1.2 mM), while GpNA was maintained at 3 mM ($K_{GPNA}$ is 1.07±0.04 mM) when glygly was varied. Inhibition by compound 3 was uncompetitive with respect to GpNA, indicating that it binds to the F form of the enzyme, that is, the covalent E-γ-glutamyl complex (FIG. 4A). The $K_i$ value obtained was 73.8±2.5 µM. Inhibition by compound 3 was competitive with respect to glygly indicating that compound 3 was occupying the acceptor site (FIG. 4B). A $K_i$ of 17.6±3.8 µM was obtained. The $K_i$ of 17.6 µM is the intrinsic value (23). The value obtained varying GpNA at a fixed glygly concentration must be the same once corrected for the concentration of fixed reactant. Given, $appK_i=K_i(1+[glygly]/K_{glygly})$, the calculated value of $K_i$ is 16.5 µM. A similar analysis of compound 3 inhibition, carried out with a highly purified preparation of human GGT expressed in yeast yielded similar results (FIG. 4C, 4D). The $appK_i$ of compound 3 as a competitive inhibitor of glygly was 25±2 µM, while that obtained varying GpNA was 58.2+1.6 µM. A fit of the data displayed in FIG. 4A-D, to the equation for noncompetitive inhibition $(v=VA/[K_a(1+I/K_{is})+A(1+I/K_{ii})])$ does give a finite, but very high $K_i$ (>200 µM) binding to the E form of the enzyme. This is not surprising since the site for glygly, and thus compound 3 must be present in E. However, the much weaker binding, >10-fold, is consistent with synergy of binding of compound 3 in the presence of the γ-glutamyl moiety.

Structure Activity Studies.

Figure 1:
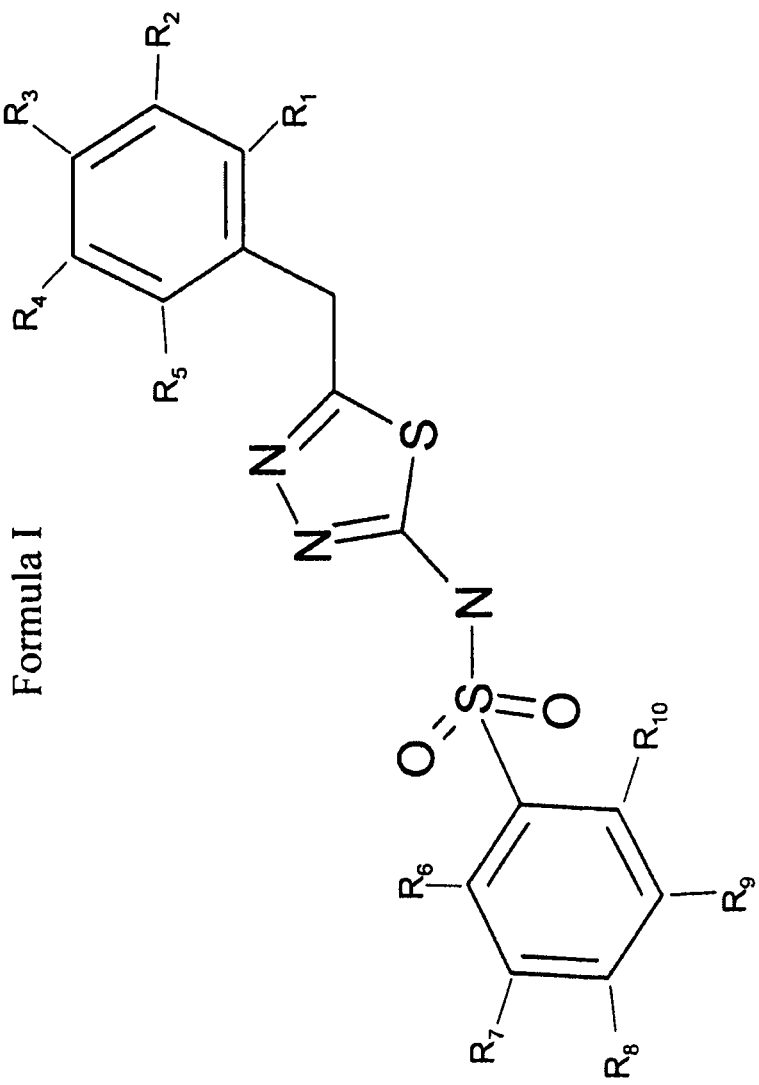
FIG. 1 shows a basic structure (Formula I) of a GGT inhibitor compound used in the methods of the present disclosure.

A series of structural analogues of compound 3 were evaluated as inhibitors of GGT. The $appK_i$ for each compound, obtained by varying GpNA, was determined experimentally with GGT isolated from human kidney (see Table 1). The general structure (Formula I) of the inhibitor containing all the essential elements is shown in FIG. 1. The $K_i$ for the unsubstituted core structure ($R_1$-$R_{10}$=H, compound 5) is 99.7±3.1 µM. Inhibition is enhanced by the substitution of either the $R_3$ or the $R_8$ positions with chlorine (FIG. 2A, Compounds 2, 4). Substitution of both the $R_3$ and the $R_8$ positions with chlorine provides the most potent inhibitor with an alpha Ki of 28.7±1.0 µM (FIG. 2A, compound 1). Addition of a methoxy group at the $R_3$ position yields the third most potent inhibitor of the analogues tested (FIG. 2A, compound 3). Substitution of the $R_8$ group position with either a methoxy compound or a nitroso group weakened the inhibition (FIG. 2B, compounds 5, 7-9).

TABLE 1

Inhibition of GGT Activity by various compounds of Formula I.

| Compound No. | Identity of R Groups | Inhibition of Transpeptidation (Alpha Ki (µM)) |
| --- | --- | --- |
| 1 | $R_3, R_8$ = Cl<br>$R_{1-2, 4-7, 9, 10}$ = H | 28.7 ± 1.0 |
| 2 | $R_3$ = Cl<br>$R_{1, 2, 4-10}$ = H | 43.3 ± 1.6 |
| 3 | $R_3$ = OCH$_3$<br>$R_{1, 2, 4-10}$ = H | 73.8 ± 2.5 |
| 4 | $R_8$ = Cl<br>$R_{1-7, 9, 10}$ = H | 75.9 ± 1.7 |
| 5 | $R_3$= Cl, $R_8$ = NO$_2$<br>$R_{1, 2, 4-7, 9, 10}$ = H | 74.3 ± 6.9 |
| 6 | $R_{1-10}$ = H | 99.7 ± 3.1 |
| 7 | $R_3$ = OCH$_3$, $R_8$ = NO$_2$<br>$R_{1, 2, 4-7, 9, 10}$ = H | 114 ± 8.4 |
| 8 | $R_3$ = OCH$_3$<br>$R_{1, 2, 4-7, 9, 10}$ = H | 226 ± 12.7 |
| 9 | $R_{3, 4, 8}$ = OCH$_3$<br>$R_{1, 2, 5-7, 9, 10}$ = H | 1,115 ± 100 |

Toxicity.

The glutamine analogues, of the prior art that inhibit GGT activity are toxic to dividing cells. We evaluated the toxicity of compound 3 and several of its structural analogues towards cells in log growth using 786-O cells, a human renal tumor cell line. Cells were grown in the presence of the test compounds for 3 days. As shown in Table 2, the glutamine analogue, acivicin, had an $LD_{50}$ of 0.81 µM. All four of the compounds tested (FIG. 2A, compounds #1, 2, 3, and FIG. 2b, compound 6) were at least an order of magnitude less toxic than acivicin. Compound 3 was more than 150-fold less toxic than acivicin. These data emphasize the reduced toxicity of GGT inhibitors that are not glutamine analogues.

Although our structure activity analysis revealed two compounds that were more potent inhibitors of GGT than compound 3 (FIG. 2A, compounds 1 and 2), these compounds were 17- to 20-fold more toxic than compound 3 making them less promising as candidates for further development for clinical use. Therefore compound 3 continued as our lead compound in further characterization studies of inhibition by this class of compounds.

TABLE 2

Toxicity of GGT Inhibitors towards Dividing 786-O Cells

| Compound | $LD_{50}$ (µM) |
|---|---|
| Acivicin | 0.81 |
| FIG. 2A Compound 1 | 7.6 |
| FIG. 2A Compound 2 | 6.5 |
| FIG. 2A Compound 3 | 128 |
| FIG. 2B Compound 6 | 71 |

Species Specificity of GGT Inhibition by Compound 3.

Figure 5:
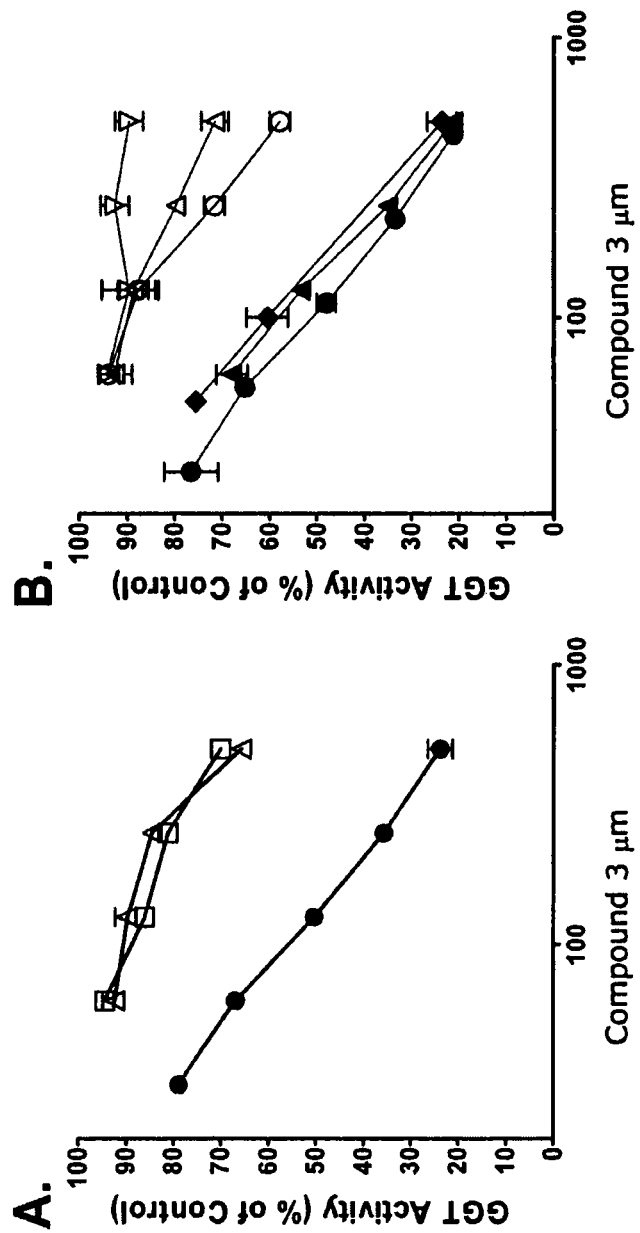
FIG. 5. Species-specific inhibition of GGT by compound 3. A, Inhibition of GGT from human kidney (●), rat kidney (Δ) and mouse kidney (□) by compound 3. Inhibition of human GGT was significantly more potent than inhibition of rat or mouse GGT (p=0.03). B, Inhibition of GGT in 786-O human renal adenocarcinoma cells (●), HK-2 normal human kidney derived cells (▲), and NIH/3T3 mouse fibroblast transfected with human GGT cDNA (◆), LLC-MK2 monkey kidney cells (○), NRK-52E rat kidney cells (△) and LLC-PK1 pig kidney (▽) cells. There was no significant difference in inhibition among the cell lines expressing human GGT, but compound 3 inhibition of GGT in human cell lines was significantly more potent than inhibition of GGT in monkey, rat or pig cell lines ($p \leq 0.04$).

Compound 3 inhibits GGT isolated from human kidney in a dose-dependent manner. However, compound 3 is 7-fold less potent as an inhibitor of GGT isolated from rat kidney and 10-fold less potent inhibiting GGT from mouse kidney (FIG. 5A). The species specificity of GGT inhibition by compound 3 was further evaluated with cells lines from five different species (FIG. 5B). Compound 3 showed dose-dependent inhibition of GGT in the two human kidney cell lines, 786-O a renal tumor cell line and HK-2, an immortalized renal proximal tubule cell line. Inhibition of GGT in the human cell lines was of similar potency to the inhibition of GGT isolated from human kidney. GGT in the rat kidney cell line NRK-52E was only weakly inhibited by compound 3, equivalent to the weak inhibition of GGT isolated from rat kidney. GGT in the pig kidney cell line LLC-PK1 was not inhibited by compound 3. GGT in the monkey kidney cell line LLC-MK2 was only weakly inhibited by compound 3 similar to the inhibition of GGT in rat kidney cells.

Figure 4:
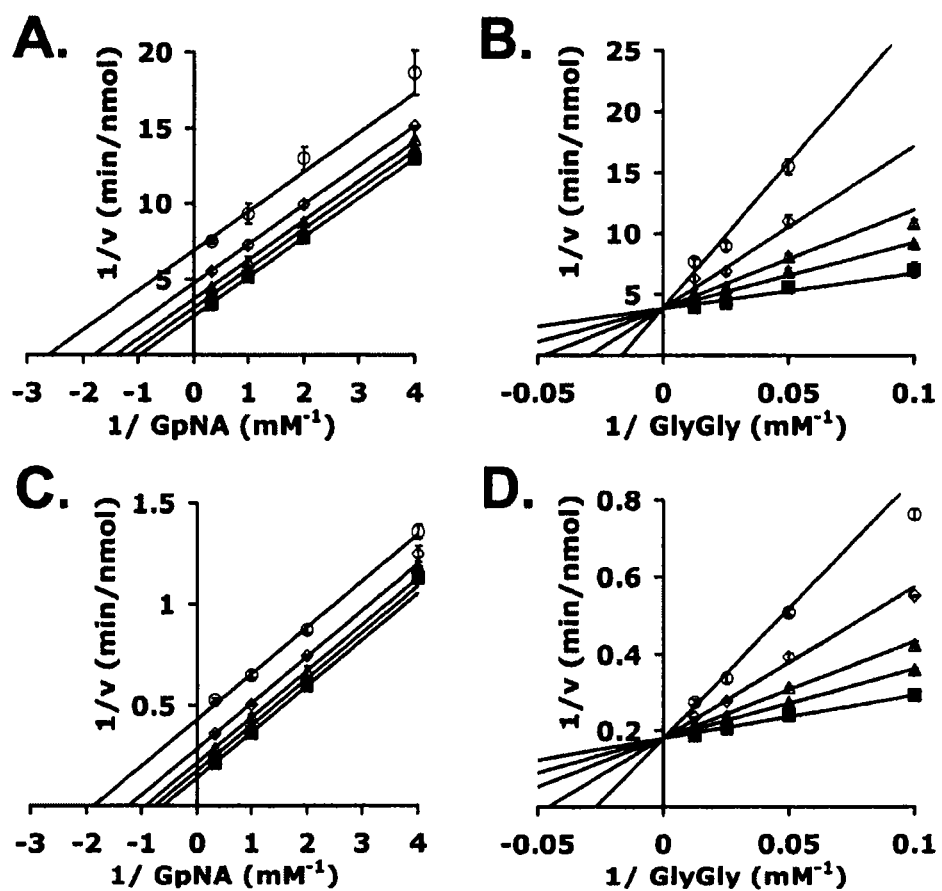
FIG. 4. Kinetic Analysis of GGT inhibition by compound 3. Double-reciprocal plots of the initial velocities of human kidney GGT (A, B) or human GGT transfected into and isolated from *Pichia pastoris* (C,D) in the presence of 40 mM glycylglycine (A,C) or 3 mM GpNA (B,D) with 0 (■), 15.2 µM (▲), 31.3 µM (Δ), 62.5 µM (◊), 125 µM (○) of compound 3. Data shown are average of triplicate values±S.D. (for many points the error bars are smaller than the symbol).

GGT is heavily glycosylated (24). To determine whether the sensitivity of GGT to inhibition by compound 3 was determined by the primary structure or by post-translational modifications such as glycosylation, we tested the sensitivity of human GGT expressed in mouse NIH/3T3 fibroblasts to inhibition by compound 3 (FIG. 5B). The data revealed that human GGT expressed in mouse cells was inhibited by compound 3 to the same extent as human GGT expressed in other human cells. Therefore the sensitivity of GGT to inhibition by compound 3 was determined by the peptide sequence rather than species-specific post-translational modifications. Data in FIG. 3 further confirm that the primary structure rather than post-translational modifications determine the degree of inhibition of GGT by compound 3. GGT isolated from human kidney (FIG. 4 A,B) is inhibited by compound 3 to the same extent as human GGT expressed in yeast (FIG. 4 C,D).

Compound 3 Inhibits the Cleavage of Glutathione by GGT.

Figure 6:
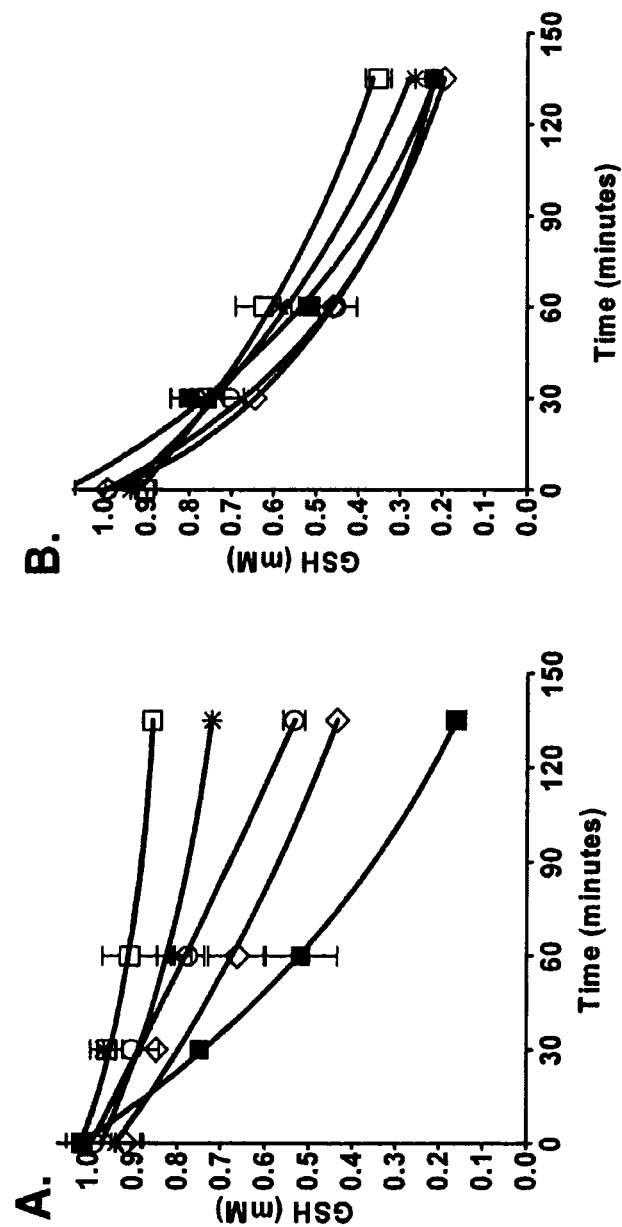
FIG. 6. Species-Specific Inhibition of glutathione degradation by compound 3. Cleavage of glutathione by human GGT (A) or rat GGT (B) in the presence of 0 (■), 62.5 uM (◇), 125 uM (○), 250 uM (★) or 500 uM (□) of compound 3. Reactions contained 1.9 mU GGT, 40 mM glycylglycine and 1 mM glutathione. Compound 3 inhibited glutathione breakdown by human GGT but did not inhibit glutathione breakdown by rat GGT.

The standard assay for GGT activity monitors the release of p-nitroaniline from the first substrate, γ-glutamyl-p-nitroanilide. To confirm that compound 3 inhibits the cleavage of glutathione, the primary physiologic substrate of GGT, we monitored the breakdown of glutathione by human, kidney GGT in the presence of the inhibitor. Compound 3 inhibited the cleavage of glutathione in a dose-dependent manner (FIG. 6A). Compound 3 also inhibited the cleavage of oxidized glutathione (GSSG) by human GGT (data not shown). To determine whether the species specificity of inhibition of GGT by compound 3 was also relevant to the physiologic substrate, compound 3 was evaluated for its ability to inhibit the degradation of glutathione by rat GGT. Rat GGT cleaved glutathione in a time dependent fashion as had been observed for human GGT (FIG. 6B). Compound 3 was unable to inhibit degradation of glutathione by GGT from rat kidney (FIG. 6B). These data corroborate the data regarding the species specificity of compound 3 obtained using the synthetic substrate, GpNA.

Discussion

We have identified a novel class of GGT inhibitors that are not glutamine analogues. Kinetic studies presently shown revealed that the mechanism of inhibition was uncompetitive relative to the γ-glutamyl substrate, indicating that the inhibitor bound the enzyme-substrate complex. In contrast, to competitive inhibitors, which lose potency as substrate concentration builds, uncompetitive inhibitors become more potent as the substrate concentration rises in an inhibited open system. Data from the GGT knockout mice show that in the absence of GGT activity, glutathione levels decrease in tissues but the concentration of glutathione in the serum rises more than 6-fold, likely due to the inability of cells to cleave glutathione and recover the amino acids (11). In addition, the glutathione concentration in the urine increases more than 2400-fold as the glutathione transits the proximal tubules intact in the absence of GGT. Westley and Westley have argued that uncompetitive inhibitors are superior to competitive inhibitors for instituting change in open systems such as those found in vivo where substrate concentrations rise with enzyme inhibition (25). Many uncompetitive inhibitors function by locking the enzyme-substrate (ES) complex in a state after initial product release but before conversion of the enzyme back to the native form. In GGT, the enzyme-substrate complex consists of the glutamyl group covalently bound to the enzyme following release of the remainder of the γ-glutamyl substrate. GGT from *E. coli* has been crystallized (26). Analysis of the crystal structure of *E. coli* GGT and the gamma-glutamyl-enzyme intermediate revealed that the N-terminal threonine of the small subunit is the catalytic nucleophile in the enzymatic reaction (27). This threonine is conserved in human, rat, mouse and pig. Site directed mutagenesis of human GGT has identified four amino acids that are essential to GGT activity (one in the large subunit, Arg 107, and three in the small subunit, Asp-423, Ser-451 and Ser-452) (28-30). All four of these amino acids are identical in human, rat, mouse and pig.

Kinetic studies on compound 3 further revealed that while binding the enzyme-γ-glutamyl complex, compound 3 occupies the acceptor site. To date, the crystal structures of GGT isolated from only *E. coli* and *H. Pylori* have been published (27; 31; 32).

Structural alterations of compound 3 increased the inhibitory activity of the compound but not without accompanying increases in toxicity. The in vitro toxicity profile of compound 3 is favorable. In a dividing cell model, compound 3 is 150-fold less toxic than acivicin which was abandoned after phase I clinical trials due to toxicity.

Without wishing to be bound by theory, it is believed that, in addition to its role in cancer therapy, GGT also plays a critical role in drug metabolism due to the ubiquitous presence of glutathione. GGT is an essential enzyme in the formation of mercapturic acids in the kidney and initiates the activation of halogenated alkenes and other drugs to potent kidney toxins through this pathway (34; 35). Cisplatin has been shown to be bioactivated to a renal toxin through the mercapturic acid pathway (36; 37). Inhibition of GGT during cisplatin-based chemotherapy would not only sensitize the tumors to the therapy, it would also block the kidney toxicity of cisplatin. Additional clinical conditions for which the GGT inhibitor of the invention have therapeutic benefit include cardiovascular disease and asthma, as nitric oxide is transported in the blood as a glutathione conjugate and requires GGT activity for its release (38; 39). Finally, GGT is one of two enzymes that metabolize leukotriene $C_4$ to leukotriene $D_4$, a mediator of inflammation common to many diseases (40) thus the GT inhibitors of the present invention can be used in a treatment to reduce inflammatory conditions.

Previous clinical studies have attempted to overcome drug resistance in tumors by inhibiting glutathione synthesis with buthionine sulfoximine (41), an inhibitor of the rate-limiting enzyme in the synthesis of glutathione. However, there was no depletion of cysteine in the body with this protocol. Cysteine's sulfur, the active nucleophilic group of the glutathione molecule, binds and inactivates reactive, electrophilic compounds. Free cysteine will also react with, and inactivate chemotherapy drugs (42). Inhibition of GGT by the compounds of the present invention reduces both intracellular glutathione and depletes cysteine levels, increasing the sensitivity of the tumor to the drug. Studies in mice have shown that inhibiting GGT for as little as 2 hr selectively lowers the intracellular cysteine concentration in GGT-positive tumors (3). Mena and colleagues used acivicin to deplete tumor GSH in combination with aggressive therapy and achieved complete cure of metastatic melanoma to the liver in 90% of test animals (4). The GGT inhibitors of the present invention thus will enhance the efficacy of cancer therapy.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, items of manufacture, compositions of matter, means, methods and steps described in the specification. As one of ordinary skill in the art will readily appreciate from the disclosure of the present invention, processes, items of manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, items of manufacture, compositions of matter, means, methods, or steps. CITED REFERENCES 1. Benlloch, M., Ortega, A., Ferrer, P., Segarra, R., Obrador, E., Asensi, M., Carretero, J., and Estrela, J. M. (2005) *J. Biol. Chem.* 280, 6950-6959.
2. Ahmad, S., Okine, L., Wood, R., Aljian, J., and Vistica, D. T. (1987) *J. Cell. Physiol.* 131, 240-246.
3. Ruoso, P. and Hedley, D. W. (2004) *Cancer Chemother. Pharmacol.* 54, 49-56.
4. Mena, S., Benlloch, M., Ortega, A., Carretero, J., Obrador, E., Asensi, M., Petschen, I., Brown, B. D., and Estrela, J. M. (2007) *Clin. Cancer Res.* 13, 2658-2666.
5. Lee, C. Y., Wey, S. P., Liao, M. H., Hsu, W. L., Wu, H. Y., and Jan, T. R. (2008) *Int. Immunopharmacol.* 8, 732-740.
6. Hanigan, M. H. and Ricketts, W. A. (1993) *Biochemistry* 32, 6302-6306.
7. Hanigan, M. H., Frierson, H. F., Jr., Swanson, P. E., and De Young, B. R. (1999) *Hum. Pathol.* 30, 300-305.
8. Hanigan, M. H., Gallagher, B. C., Townsend, D. M., and Gabarra, V. (1999) *Carcinogenesis* 20, 553-559.
9. Ahluwalia, G. S., Grem, J. L., Hao, Z., and Cooney, D. A. (1990) *Pharmacol. Ther.* 46, 243-271.
10. Lyons, S. D., Sant, M. E., and Christopherson, R. I. (1990) *J. Biol. Chem.* 265, 11377-11381.
11. Lieberman, M. W., Wiseman, A. L., Shi, Z., Carter, B. Z., Barrios, R., Ou, C., Chevez-Barrios, P., Wand, Y., Habib, G. M., Goodman, J. C., Huang, S. L., Lebovitz, R. M., and Matzuk, M. M. (1996) *Proc. Natl. Acad. Sci. USA* 93, 7923-7926.
12. Folk, J. E. (1969) *J. Biol. Chem.* 244, 3707-3713.
13. Tate, S. S. and Meister, A. (1978) *Proc. Natl. Acad. Sci. USA* 75, 4806-4809.
14. Lherbet, C., Gravel, C., and Keillor, J. W. (2004) *Bioorg. Med. Chem. Lett.* 14, 3451-3455.
15. Lherbet, C. and Keillor, J. W. (2004) *Org. Biomol. Chem.* 2, 238-245.
16. Han, L., Hiratake, J., Kamiyama, A., and Sakata, K. (2007) *Biochemistry* 46, 1432-1447.
17. Han, L., Hiratake, J., Tachi, N., Suzuki, H., Kumagai, H., and Sakata, K. (2006) *Bioorg. Med. Chem.* 14, 6043-6054.
18. Taylor, S. A., Crowley, J., Pollocck, T. W., Eyre, H. J., Jaeckle, C., Hynes, H. E., and Stephens, R. L. (1991) *J. Clin. Oncol.* 9, 1476-1479.
19. Orlowski, M. and Meister, A. (1963) *Biochim. Biophys. Acta* 73, 679-681.
20. Hansen, M. B., Nielsen, S. E., and Berg, K. (1989) *J. Immunol. Methods* 119, 203-210.
21. Tietze, F. (1969) *Anal. Biochem.* 27, 502-522
22. Lipinski, C. A., Lombardo, F., Dominy, B. W., and Feeney, P. J. (2001) *Adv. Drug Deliv. Rev.* 46, 3-26.
23. Cook, P. F. and Cleland, W. W. (2007) *Enzyme Kinetics and Mechanisms*, Garland Press, London.
24. Yamashita, K., Hitoi, A., Matsuda, Y., Miura, T., Katunuma, N., and Kobata, A. (1986) *J. Biochem. (Tokyo)* 99, 55-62.
25. Westley, A. M. and Westley, J. (1996) *J. Biol. Chem.* 271, 5347-5352.
26. Kumagai, H., Nohara, S., Suzuki, H., Hashimoto, W., Yamamoto, K., Sakai, H., Sakabe, K., Fukuyama, K., and Sakabe, N. (1993) *J. Mol. Biol.* 234, 1259-1262.
27. Okada, T., Suzuki, H., Wada, K., Kumagai, H., and Fukuyama, K. (2006) *Proc. Natl. Acad. Sci. U.S.A* 103, 6471-6476.
28. Ikeda, Y., Fujii, J., Anderson, M. E., Taniguchi, N., and Meister, A. (1995) *J. Biol. Chem.* 270, 22223-22228.
29. Ikeda, Y., Fujii, J., Taniguchi, N., and Meister, A. (1995) *J. Biol. Chem.* 270, 12471-12475.
30. Ikeda, Y., Fujii, J., and Taniguchi, N. (1993) *J. Biol. Chem.* 268, 3980-3985.
31. Morrow, A. L., Williams, K., Sand, A., Boanca, G., and Barycki, J. J. (2007) *Biochemistry* 46, 13407-13414.
32. Boanca, G., Sand, A., Okada, T., Suzuki, H., Kumagai, H., Fukuyama, K., and Barycki, J. J. (2007) *J. Biol. Chem.* 282, 534-541.
33. Allison, R. D. (1985) *Methods Enzymol.* 113, 419-437.
34. Anders, M. W. and Dekant, W. (1998) *Annual Review of Pharmacology and Toxicology* 38, 501-537.
35. Bai, F., Jones, D. C., Lau, S. S., and Monks, T. J. (2001) *Chem. Res. Toxicol.* 14, 863-870.
36. Hanigan, M. H., Gallagher, B. C., Taylor, P. T. Jr., and Large, M. K. (1994) *Cancer Res.* 54, 5925-5929.
37. Hanigan, M. H., Lykissa, E. D., Townsend, D. M., Ou, C. N., Barrios, R., and Lieberman, M. W. (2001) *Am. J. Pathol.* 159, 1889-1894.

38. Henson, S. E., Nichols, T. C., Holers, V. M., and Karp, D. R. (1999) *J. Immunol.* 163, 1845-1852.
39. Lipton, A. J., Johnson, M. A., Macdonald, T., Lieberman, M. W., Gozal, D., and Gaston, B. (2001) *Nature* 413, 171-174.
40. Carter, B. Z., Wiseman, A. L., Orkiszewski, R., Ballard, K. D., Ou, C. N., and Lieberman, M. W. (1997) *J. Biol. Chem.* 272, 12305-12310.
41. O'Dwyer, P. J., Hamilton, T. C., Young, R. C., LaCreta, F. P., Carp, N., Tew, K. D., Padavic, K., Comis, L., and Ozols, R. F. (1992) *J. Natl. Cancer Inst.* 84, 264-267.
42. Bose, R. N., Ghosh, S. K., and Moghaddas, S. (1997) *J. Inorg. Biochem.* 65, 199-205.

Each of the references, patents or publications cited herein is expressly incorporated by reference in its entirety.

What is claimed is:

1. A method of inhibiting human gamma-glutamyl transpeptidase (GGT), comprising:
   obtaining a compound as represented by Formula (I), or a pharmaceutically acceptable salt thereof:

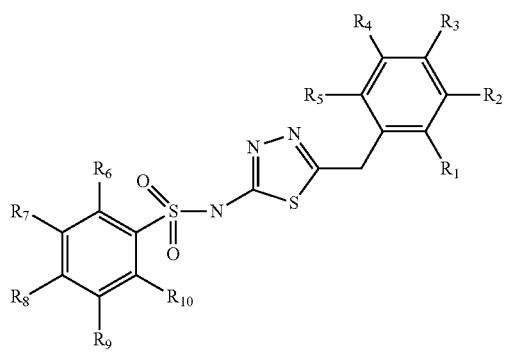

(I)

wherein $R_1$-$R_{10}$ are the same or different from each other and represent H, Cl, F, Br, I, OH, an alkoxy, or $NO_2$; and
exposing the compound to the human GGT thereby inhibiting activity of the human GGT.

2. The method of claim 1 wherein the alkoxy of Formula (I) is selected from the group comprising methoxy, ethoxy, n-propoxy, iso-propoxy, n-butoxy, tert-butoxy, sec-butoxy, a pentoxy, a hexoxy, a octoxy, a nonoxy, a decoxy, a undecoxy, and a dodecoxy.

3. The method of claim 1 wherein at least one of $R_1$-$R_{10}$ is Cl.

4. The method of claim 1 wherein at least one of $R_1$-$R_{10}$ is an alkoxy group.

5. The method of claim 4 wherein the alkoxy group is a methoxy group or an ethoxy group.

6. The method of claim 1 wherein $R_3$ is a methoxy group and $R_1$, $R_2$, and $R_4$-$R_{10}$ are H.

7. The method of claim 1 wherein $R_3$ is a methoxy group and at least one of $R_7$ and $R_9$ is Cl.

8. The method of claim 1 wherein $R_3$ is a methoxy group, at least one of $R_7$ and $R_9$ is Cl, and $R_1$, $R_2$, $R_4$-$R_6$, $R_8$, and $R_{10}$ are H.

9. The method of claim 1 wherein $R_3$ is a methoxy group, $R_7$ is Cl, and $R_1$, $R_2$, $R_4$-$R_6$, and $R_8$-$R_{10}$ are H.

10. The method of claim 1 wherein $R_3$ is a methoxy group, $R_9$ is Cl, and $R_1$, $R_2$, $R_4$-$R_8$, and $R_{10}$ are H.

11. A method of inhibiting human gamma-glutamyl transpeptidase (GGT), comprising:
    obtaining a compound as represented by Formula (I), or a pharmaceutically acceptable salt thereof:

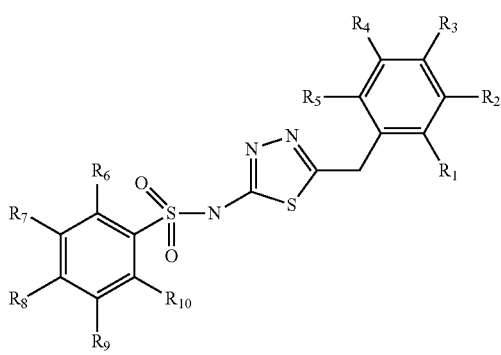

(I)

wherein $R_3$ is a methoxy group and $R_1$, $R_2$, and $R_4$-$R_{10}$ are H; and
exposing the compound to the human GGT thereby inhibiting activity of the human GGT.

12. A method of inhibiting human gamma-glutamyl transpeptidase (GGT) in vitro, comprising:
    obtaining a compound as represented by Formula (I), or a pharmaceutically acceptable salt thereof:

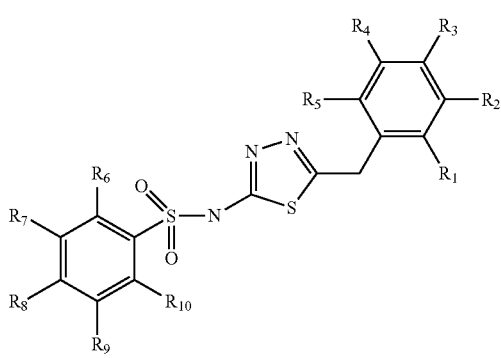

(I)

wherein $R_1$-$R_{10}$ are the same or different from each other and represent H, Cl, F, Br, I, OH, an alkoxy, or $NO_2$; and
exposing the compound to the human GGT in vitro, thereby inhibiting activity of the human GGT.

13. The method of claim 12 wherein the alkoxy of Formula (I) is selected from the group comprising methoxy, ethoxy, n-propoxy, iso-propoxy, n-butoxy, tert-butoxy, sec-butoxy, a pentoxy, a hexoxy, a octoxy, a nonoxy, a decoxy, a undecoxy, and a dodecoxy.

14. The method of claim 12 wherein at least one of $R_1$-$R_{10}$ is Cl.

15. The method of claim 12 wherein at least one of $R_1$-$R_{10}$ is an alkoxy group.

16. The method of claim 15 wherein the alkoxy group is a methoxy group or an ethoxy group.

17. The method of claim 12 wherein $R_3$ is a methoxy group and $R_1$, $R_2$, and $R_4$-$R_{10}$ are H.

18. The method of claim 12 wherein $R_3$ is a methoxy group and at least one of $R_7$ and $R_9$ is Cl.

19. The method of claim 12 wherein $R_3$ is a methoxy group, at least one of $R_7$ and $R_9$ is Cl, and $R_1$, $R_2$, $R_4$-$R_6$, $R_8$, and $R_{10}$ are H.

20. The method of claim 12 wherein $R_3$ is a methoxy group, $R_7$ is Cl, and $R_1$, $R_2$, $R_4$-$R_6$, and $R_8$-$R_{10}$ are H.

21. The method of claim 12 wherein $R_3$ is a methoxy group, $R_9$ is Cl, and $R_1$, $R_2$, $R_4$-$R_8$, and $R_{10}$ are H.

22. A method of inhibiting human gamma-glutamyl transpeptidase (GGT), comprising:

obtaining a compound as represented by Formula (I), or a pharmaceutically acceptable salt thereof:

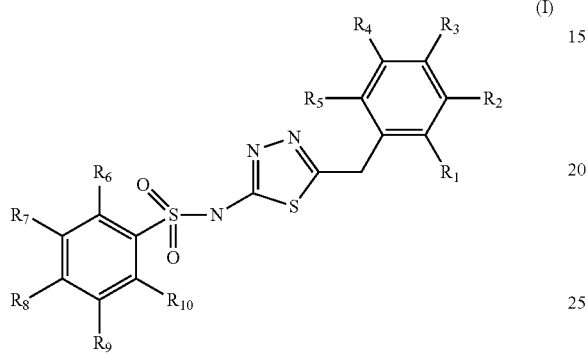

wherein $R_3$ is a methoxy group, at least one of $R_7$ and $R_9$ is Cl, and $R_1$, $R_2$, $R_4$-$R_6$, $R_3$, and $R_{10}$ are H; and exposing the compound to the human GGT, thereby inhibiting activity of the human GGT.

* * * * *

UNITED STATES PATENT AND TRADEMARK OFFICE
CERTIFICATE OF CORRECTION

PATENT NO. : 8,741,937 B2
APPLICATION NO. : 13/428224
DATED : June 3, 2014
INVENTOR(S) : Hanigan It is certified that error appears in the above-identified patent and that said Letters Patent is hereby corrected as shown below:

Title Page:
Under Item [54] and in the Specification, Column 1, line 1: After "GAMMA" insert a hyphen -- - --

In the Specification:
Column 8, line 59: Delete "amifostine;" and replace with -- arnifostine; --

Column 16, line 52: Delete "cortico steroids" and replace with -- corticosteroids --

In the Claims:
Column 30, line 28, Claim 12: Delete "in vitro," and replace with -- *in vitro*, --

Column 30, line 51, Claim 12: Delete "in vitro," and replace with -- *in vitro*, --

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,741,937 B2  Page 1 of 1
APPLICATION NO. : 13/428224
DATED : June 3, 2014
INVENTOR(S) : Marie H. Hanigan It is certified that error appears in the above-identified patent and that said Letters Patent is hereby corrected as shown below:

In the Specification

Column 8,
line 59, "arnifostine;" (as changed to read in the Certificate of Correction issued August 5, 2014) is deleted and text is returned to its original state as it appears in printed patent to read --amifostine;--.

Signed and Sealed this
Twenty-sixth Day of August, 2014

Michelle K. Lee
*Deputy Director of the United States Patent and Trademark Office*